US006534291B1

(12) United States Patent
Duvick et al.

(10) Patent No.: US 6,534,291 B1
(45) Date of Patent: Mar. 18, 2003

(54) COMPOSITIONS AND METHODS FOR FUMONISIN DETOXIFICATION

(75) Inventors: Jon Duvick, Des Moines, IA (US); Joyce Maddox, Des Moines, IA (US); Jacob Gilliam, Norwalk, IA (US); Otto Folkerts, Guilford, CT (US); Oswald R. Crasta, Branford, CT (US)

(73) Assignees: Pioneer Hi-Bred International, Inc., Des Moines, IA (US); CuraGen Corporation, New Haven, CT (US)

(*) Notice: Subject to any disclaimer, the term of this patent is extended or adjusted under 35 U.S.C. 154(b) by 85 days.

(21) Appl. No.: 09/677,682

(22) Filed: Oct. 2, 2000

Related U.S. Application Data

(62) Division of application No. 09/351,224, filed on Jul. 12, 1999, now Pat. No. 6,388,171.

(51) Int. Cl.$^{7}$ ............................ C12N 1/20; C12N 9/16; C12N 9/14; C12P 21/02

(52) U.S. Cl. ................ 435/71.1; 435/252.3; 435/320.1; 435/196; 536/23.1; 536/23.2; 536/24.1; 424/93.1

(58) Field of Search ........................... 435/252.3, 320.1, 435/71.1, 196; 536/23.1, 23.2, 24.1; 424/93.1

(56) References Cited

U.S. PATENT DOCUMENTS

| | | | |
|---|---|---|---|
| 5,178,863 | A | 1/1993 | Toyoda et al. |
| 5,639,949 | A | 6/1997 | Ligon et al. |
| 5,716,820 | A | 2/1998 | Duvick et al. |
| 5,792,931 | A | 8/1998 | Duvick et al. |
| 5,877,273 | A | 3/1999 | Hance et al. |

FOREIGN PATENT DOCUMENTS

| | | |
|---|---|---|
| EP | 0712932 A2 | 5/1996 |
| WO | WO 95/06121 | 3/1995 |
| WO | WO 95/06128 | 3/1995 |
| WO | WO 96/06175 | 2/1996 |
| WO | WO 96/12414 | 5/1996 |
| WO | WO 96/20595 | 7/1996 |
| WO | WO 99/02703 | 1/1999 |
| WO | WO 99/10514 | 3/1999 |
| WO | WO 99/32505 | 7/1999 |

OTHER PUBLICATIONS

Keller and Sullivan, J. Agric. Food Chem. (1998) 46:2823–2826.*

Anzai et al. (1989) "Transgenic Tobacco Resistant To A Bacterial Disease By The Detoxification Of A Pathogenic Toxin",*Mol Gen Genet 219*:492–494, ISSN: 0026–3924, XP002083624.

Anzai et al. (Jan. 1, 1989) "Transgenic tobacco resistant to a bacterial disease by the detoxification of a pathogenic toxin",*Molecular and General Genetics 219*:492–494, XP002083624, ISSN: 0026–3925 the whole document.

Armengaud (Sep. 17, 1998) "Shingomonas sp. ORFs G1, G3 to G8 and EDO2gene", EMBL Accession No:AJ223219, XP002133317, see nts 3310–4600.

Armengaud (Nov. 1, 1998) "Flavin–binding monooxygenase–like", PFAM Accession No:PF00743, XP002133310.

Armengaud (Nov. 1, 1998) "Putative Monooxygenase", SWISSPROT Accession No:086908, XP002133318.

Bedzyk et al. (Jun. 15, 1993) "*Paracoccus denitrificans* electron transfer flavoprotein alpha and beta subunit genes, complete cd's.", EMBL Accession No:L14864, XP002130956 the whole document.

Bennetzen et al. (1992) "Approaches and Progress in the Molecular Cloning of Plant Disease Resistance Genes", *Genetic Engineering 14*:99–124.

Bergeron et al. (Dec. 4, 1997) "*Xanthobacter autotrophicus* transcriptional activator AldR (aldR) gene, partial cds.; and AND–dependent chloroacetaldehyde dehydrogenase (aldB) gene, complete cds", EMBL Accession No:AF029734, XP002121099, see reverse complement of sequence 2447–2066.

Bergeron et al. (Jan. 19, 1998) "Cloning, sequence and expression of a linear plasmid–based and a chromosomal homolog of chloroacetaldehyde dehydrogenase–encoding genes in*Xanthobacter autotrophicus* GJ10", *Gene 207*:9–18, XP002121100.

Blackwell et al. (1999) Oxidative Deamination of Hydrolyzed Fumonisin $B_1$ ($AP_1$) by Cultures of *Exophiala spiniferd, Natural Toxins 7*(*1*):31–38, ISSN: 1056–9014, XP002121276.

Blattner et al. (Oct. 1, 1996) "Hypothetical transcriptional regulator in MODC–BIOA intergenic region", SWISSPROT Accession No:p52696, XP002121103 the whole document.

Blattner et al. (Jan. 29, 1997) "*Escherichia coli* K–12 MG1655 section 69 of 400 of the complete genome", EMBL Accession No:AE000179, XP002122134 see complement (4647..5653).

Bowen et al. (May 5, 1997) "Cloning and Phylogenetic Analysis of the Genes Encoding Acetohydroxyacid Synthase from the Archaeon *methanococcus aeolicus", Gene 188*:77–84, XP002130949 figure 2 and EMBL Accession No:U35458 (May 5, 1997).

(List continued on next page.)

*Primary Examiner*—James Ketter
*Assistant Examiner*—Daniel M. Sullivan
(74) *Attorney, Agent, or Firm*—Alston & Bird LLP

(57) ABSTRACT

Compositions and methods for the complete detoxification of fumonisin and fumonisin degradation products are provided. Particularly, nucleotide sequences corresponding to the detoxification enzymes are provided. The sequences find use in preparing expression cassettes for the transformation of a broad variety of host cells and organisms.

21 Claims, 2 Drawing Sheets

OTHER PUBLICATIONS

Chattopadhyay et al. (1994) "Molecular Cloning And Sequencing Of An Operon, carRSOf *Azospirillum brasilense,* That Codes For A Novel Two–Component Regulatory System: Demonstration Of A Positive Regulatory Role OfcarR For Global Control Of Carbohydrate Catabolism",*Journal of Bacteriology 176(24)*:7484–7490.

Chattopadhyay et al. (1996) "CarR Gene", TREMBL Accession No: Q43901, XP002121105.

Chen et al. (Apr. 2, 1988) "*Homo sapiens* P–glycoprotein (PGY1) mRNA, complete cds.", EMBL Accession No. M14758, Abstract No. XP002138295, SWISSPROT Accession No. P08183 (Aug. 1, 1988).

Chen et al. (Jul. 16, 1988) "Acinetobacter sp. Cyclohexanone monooxygenase gene, complete cds", EMBL Accession No:M19029, XP002133308.

Chen et al. (Oct. 1, 1998) "Cyclohexanone Monooxygenase (EC 1.14.13.22)", SWISSPROT Accession No:P12015, XP002133309.

Chen et al. (Oct., 1, 1989) "Flavin–binding monooxygenase–like", PFAM Accession No.:PF00743, XP002133310.

Chudhary et al. (Jun. 6, 1998) "483PLA2 Cosmid library of chromosome II *Rhodobacter sphaeroides* genomic clone 483PLA2, genomic survey sequence", EMBL Accession No:AQ012082, XP002130954, the whole document.

Cole et al. (May 10, 1996) "*Mycobacterium tuberculosis* H37Rv complete genome; segment 41/162", EMBL Accession No:Z73101, XP002130945, the whole document and "Probable Monooxygenase RV0892 (EC 1.14.13.*)," SWISSPROT Accession No:Q10532 (Oct. 1, 1996).

Cole et al. (Nov. 9, 1997) "*Mycobacterium tuberculosis* H37Rv complete genome; segment 125–162", EMBL Accession No:AL008883, XP002121098, see sequence 1434–1843.

Cole et al. (Jan. 15, 1998) "*Mycobacterium tuberculosis* H37Rv complete genome; segment 132/162", EMBL Accession No:AL021287, XP002130944, the whole document and TREMBL Accession No:053294, (Jun. 1, 1998).

Cole et al. (Feb. 22, 1998) "*Mycobacterium tuberculosis* H37Rv complete genome; segment 33/162", EMBL Accession No:AL021943, XP002130936, the whole document.

Cole et al. (Feb. 22, 1998) "*Mycobacterium tuberculosis* H37Rv complete genome; segment 29/162", EMBL Accession No:AL021942, XP002130940, the whole document.

Cole et al. (Mar. 12, 1998) "*Mycobacterium tuberculosis* H37Rv complete genome; segment 155/162", EMBL Accession No:AL022121, XP002130947, the whole document.

Coulton et al. (Nov. 18, 1996) "*E. coli* fhuA, fhuC and fhuD genes encoding the ferrichrome–iron receptor and two ferric aerobactin and ferric coprogen transport proteins, complete cds.", EMBL Accession No:M12486, XP002130941, the whole document.

Coulton et al. (Apr. 1, 1988) "Ferrichrome–Iron Receptor Precursor (Ferric Hydroxamate Uptake)", SWISSPROT Accession No:P06971, XP002130942.

Database Biosis 'Online!' Biosciences Information Service (1996) "Styrene metabolism in cytochrome P–450–dependent styrene monoxygenase", Database Accession No. PREV199698822892, Abstract No. XP002138296; and *Applied and Environmental Microbiology* (1996) vol. 62, No. 4, pp. 1471–1474.

DU (Dec. 15, 1996) "*Mycobacterium tuberculosis* sequence from clone y175", EMBL Accession No:AD000015, XP002121097, see sequence 6027–6064.

Duvick et al. (1998) "Detoxification Of MycotoxinsIn Planta As A Strategy For Improving Grain Quality and Disease Resistance: Identification Of Fumonisin–Degrading Microbes From Maize",*Molecular Genetics of Host–Specific Toxins In Plant Disease,* Proceedings of the 3$^{rd}$ Tottori International Symposium Daisen, Tottori, Japan Aug. 24–29, 1997, pp. 369–381, ISBN: 0–7923–4981–4, 1998, XP002121275.

Freiberg et al. (Oct. 1, 1996) "Putative transcriptional regulator Y4SM (ORF–1)", SWISSPROT Accession No:P50337, XP002121106, the whole document.

Ghosh et al. (Jan. 30, 1995)"*A. brasilense* carR gene", EMBL Accession No:X70360, XP002122135 the whole document and Chattophadyayet al. (Nov. 1, 1996) "CarR Gene", TREMBL Accession NO:Q43901, XP002121105 the whole document.

Heller et al. (Nov. 18, 1996) "*E. coli* btuB gene for the vitamin B12 receptor protein BtuB", EMBL Accession No:M10112, XP002130934, the whole document and SWISSPROT Accession No:P06129, (Jan. 1, 1998).

Iimura (May 31, 1995) "Msx–2 homolog ([human, dental pulp–derived cells, mRNA, 2065 nt]", EMBL Accession No:S75361, XP002130932, the whole document.

Ishiguro et al. (Apr. 22, 1989) "Transposon Tn4311 (from *E. coli* K–12) citrate utilization protein citA and citB genes, complete cds.", EMBL Accession No:M22041, XP002130953, the whole document.

Ishihara et al., AB#006450.

Itagaki et al. (Jan. 2, 1998) "*Rhodococcus rhodochrous* gene for steroid monooxygenase, complete cds", EMBL Accession No:AB010439, XP002133311.

Kim et al. (Feb. 4, 1998) "Organization and transcriptional characterization of the $cat_1$ gene cluster in *Acinetobacter iwoffi* K24", *Biochemical and Biophysical Research Communications 243*289–294, XP002121104 see fig. 2 and fig. 3 ORFR1.

Klenk et al. (Dec. 1, 1997) "*Archaeoglobus fulgidus* section 144 of 172 of the complete genome", EMBL Accession No:AE000963, XP002130948, the whole document.

Linthorst et al. (1989) "Constitutive Expression of Pathogenesis–Related Proteins PR–1, GRP, and PR–S in Tobacco Has No Effect on Virus Infection", *The Plant Cell 1*:285–291.

Madhusudhan et al. (Jul. 24, 1991) "*Pseudomonas putida* branched–chain keto acid dehydrogenase operon (bkdA1, bkdA1 and bkdA2), transacylase E2 bkdB), bkdR and lipoamide dehydrogenase (lpdV) genes, complete cds," EMBL Accession No:M57613, XP002121102, see reverse complement of sequence 1405–1010.

Madhusudhan et al. (Nov. 1, 1995) "Bkd operon transcriptional regulator", SWISSPROT Accession No:P42179, XP002121107, the whole document.

Martinez–Salazar et al. (Apr. 1996) "Characterization of the Genes Coding for the Putative Sigma Factor AlgU and Its Regulators MucA,, MucB, MucC, and MucD in*Azotobacter vinelandii*and Evaluation of Their Roles in Alginate Bioosynthesis",*Journal of Bacteriology 178(7)*:1800–1808, XP002130939.

Molnar et al. (Oct. 29, 1992) "Streptomyces sp. Genes for hypothetic proteins", EMBL Accession No:D13457, XP002130955 the whole document.

Morii et al. (Jun. 1, 1998) "Flavin–binding monooxygenase–like" PFAM Accession No.:PF00743, XP002133310.

Morii et al. (Jun. 1, 1998) "Steroid Monooxygenase", SWISSPROT Accession No:050641, XP002133312.

Murakami et al. (Jan. 21, 1999) "Cloning And Sequence Analysis Of Two Catechol–Degrading Gene Clusters From The Aniline–Assimilating Bacterium Frateuria Species ANA–18", *Gene* 226(2):189–198.

Murphy et al. (Jan. 26, 1998) "*Streptomyces coelicolor* cosmid 10A5", EMBL Accession No:AL021529, XP002121096, see reverse complement of 20673–20430.

Nikawa et al. (Nov. 21, 1990) "*Saccharomyces cerevisiae* choline transport gene, complete cds.", EMBL Accession No. J05603, Abstract No. XP002138294, SWISSPROT Accession No. P19807 (Jul. 15, 1998).

Oliver et al. (May 27, 1998) "Streptomyces cosmid IC3," EMBL Accession No:AL023702, XP002130938, the whole document.

PCT Invitation To Pay Additional Fees, mailed Mar. 30, 2000, International Application No. PCT/US99/15824, International Filing Date Jul. 14, 1999.

Pealing et al. (Nov. 3, 1992), "*Shewanella putrefaciens* flavocytochrome c gene, complete cds.", EMBL Accession No:L04283, XP002130951, the whole document.

Peng et al. (Jul. 1998) "Cloning of a*Sphingomonas paucimobilis*SYK–6 Gene Encoding a Novel Oxygenase That Cleaves Lignin–Related Biphenyl and Characterization of the Enzyme",*Applied and Environmental Microbiology* 64(7):2520–2527, XP002130935.

Perrett et al. (Aug. 4, 1993) "Rhizobium sp. ORF–1 and ORF–2", EMBL Accession No:X74314, XP002121101, sequence 463–852.

Peterson et al. (1992) "Cytochrome P–450terp. Isolation and Purification of the Protein and Cloning and Sequencing of Its Operon",*Journal of Biological Chemistry* 267(20).14193–14203, XP002130946 figures 4, 8 and EMBL Accession No:M91440 (Apr. 17, 1992), and "Probable aldehyde dehydrogenase (EC 1.2.1.3)" SWISSPROT Accession No:P33008 (Oct. 1, 1993).

Plunkett et al. (Dec. 30, 1994) "*Escherichia coli* K–12 chromosomal region from 67.4 to 76.0 minutes", EMBL Accession No:U18997, XP002130937, the whole document.

Rakin et al. (1994) "The Pesticin Receptor of *Yersinia enterocolitica*: A Novel Virulence Factor With Dual Function",*Molecular Microbiology* 13 (2l):253–263.

Schaap et al. (Jul. 24, 1998) "*Agaricus bisporus* aldA and echA genes", EMBL Accession No. Y17825, Abstract No. XP002138292.

Schmidt et al. (1990) "Cloning and Nucleotide Sequence Of ThecrtI Gene Encoding Phytoene Dehydrogenase From The CyanobacteriumAphanocapsa PCC6714", *Gene* 91(1):113–117.

Seebacher et al. (Oct. 17, 1996) "*R. norvegicus* mRNA for laminin chain, 765bp", EMBL Accession No:Y08882, XP002130943, the whole document.

Seeger (Jul. 2, 1998) "*Streptomyces coelicolor* cosmid 8A6", EMBL Accession No.:AL031013, XP002130933, the whole document.

Van der Rest (Apr. 4, 1990) "*Klebsiella pneumoniae* cit(+) gene for citrate carrier protein", EMBL Accession No:X51479, XP002130931, the whole document.

Vlcek et al. (May 13, 1998) "*Rhodobacter capsulatus* strain SB1003, partial genome", EMBL Accession No:AF010496, XP002130950, the whole document.

Walczak et al. (Jul. 14, 1998) "*Streptomyces griseus* subsp. *Griseus* nonactin biosynthesis gene cluster, partial sequence", EMBL Accession No:AF074603, XP002130952, the whole document.

Wang et al. (May 15, 1996) "*Pseudomonas putida* p–cymene catabolism (cym) and p–cumate catabolism (cmt) operons and enol–coenzyme A hydratase gene, complete cds.", EMBL Accession No. U24215, Abstract No. XP002138293, SPTREMBL Accession No. 033455 (Jan. 1, 1995).

Willins et al. (Aug. 4, 1990) "*E. coli* leucine–responsive–regulatory protein (Lrp) gene, complete cds.", EMBL Accession No:M35869, XP002122136 see sequence 1..495 and Willinsetal. (Feb. 1, 1991) "Leucine–responsive regulatory protein", SWISSPROT Accession No:P19494, XP002121108 the whole document.

Willins et al. (1991) "Leucine–Responsive Regulatory Protein", SWISSPROT Accession No. P19494, XP002121108.

Willins et al. (1991) "Characterization Of Lrp, and *Escherichia coli* Regulatory Protein That Mediates A Global Response To Leucine", *The Journal of Biological Chemistry* 266(17).10768–10774.

\* cited by examiner

US 6,534,291 B1

COMPOSITIONS AND METHODS FOR FUMONISIN DETOXIFICATION

CROSS-REFERENCE TO RELATED APPLICATIONS

This Application is a Divisional Application of U.S. patent application Ser. No. 09/351,224, filed Jul. 12, 1999 issued as U.S. Pat. No. 6,388,171, herein incorporated by reference.

FIELD OF THE INVENTION

The invention relates to compositions and methods for detoxification or degradation of fumonisin or AP1. The method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides, and improved agricultural practices. However, as any grower or home gardener can attest, the problems of fungal plant disease continue to cause difficulties in plant cultivation. Thus, there is a continuing need for new methods and materials for solving the problems caused by fungal diseases of plants.

These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. In the case of pathogens that produce toxins that are undesirable to mammals or other animals that feed on the crop plants, interference with toxin production, storage, or activity can be beneficial.

Since their discovery and structural elucidation in 1988 (Bezuidenhout et al. (1988) *Journal Chem. Soc., Chem. Commun.* 1988:743–745), fumonisins have been recognized as a potentially serious problem in maize-fed livestock. They are linked to several animal toxicoses including leukoencephalomalacia (Marasas et al. (1988) *Onderstepoort J. Vet. Res.* 55:197–204; Wilson et al. (1990) *American Association of Veterinary Laboratory Diagnosticians: Abstracts 33rd Annual Meeting,* Denver, Colo., Madison, Wis., USA) and porcine pulmonary edema (Colvin et al. (1992) *Mycopathologia* 11 7:79–82). Fumonisins are also suspected carcinogens (Geary et al. (1971) *Coord. Chem. Rev.* 7:81; Gelderblom et al. (1991) *Carcinogenesis* 12:1247–1251; Gelderblom et al. (1992) *Carcinogenesis* 13:433–437). Fusarium isolates in section Liseola produce fumonisins in culture at levels from 2 to >4000 ppm (Leslie et al. (1992) *Phytopathology* 82:341–345). Isolates from maize (predominantly mating population A) are among the highest producers of fumonisin (Leslie et al., supra). Fumonisin levels detected in field-grown maize have fluctuated widely depending on location and growing season, but both pre-harvest and postharvest surveys of field maize have indicated that the potential for high levels of fumonisins exists (Murphy et al. (1993) *J. Agr. Food Chem.* 41:263–266). Surveys of food and feed products have also detected fumonisin (Holcomb et al. (1993) *J. Agr. Food Chem.* 41:764–767; Hopmans et al. (1993) *J. Agr. Food Chem.* 41:1655–1658); Sydenham et al. (1991) *J. Agr. Food Chem.* 39:2014–2018). The etiology of Fusarium ear mold is poorly understood, although physical damage to the ear and certain environmental conditions can contribute to its occurrence (Nelson et al. (1992) *Mycopathologia* 117:29–36). Fusarium can be isolated from most field grown maize, even when no visible mold is present. The relationship between seedling infection and stalk and ear diseases caused by Fusarium is not clear. Genetic resistance to visible kernel mold has been identified (Gendloff et al. (1986) *Phytopathology* 76:684–688; Holley et al. (1989) *Plant Dis.* 73:578–580), but the relationship to visible mold to fumonisin production has yet to be elucidated.

Fumonisins have been shown to in in vitro mammalian cell studies to inhibit sphingolipid biosynthesis through inhibition of the enzyme sphingosine N-acetyl transferase, resulting in the accumulation of the precursor sphinganine (Norred et al. (1992) *Mycopathologia* 117:73–78; Wang et al. (1991) *Biol. Chem.* 266:14486; Yoo et al. (1992) *Toxicol. Appl. Pharmacol.* 114:9–15; Nelson et al. (1993) *Annu. Rev. Phytpathol.* 31:233–252). It is likely that inhibition of this pathway accounts for at least some of fumonisin's toxicity, and support for this comes from measures of sphinganine:sphingosine ratios in animals fed purified fumonisin (Wang et al. (1992) *J. Nutr.* 122:1706–1716). Fumonisins also affect plant cell growth (Abbas et al. (1992) *Weed Technol.* 6:548–552; Van Asch et al. (1992) *Phytopathology* 82:1330–1332; Vesonder et al. (1992) *Arch. Environ. Contam. Toxicol.* 23:464–467). Kuti et al. (1993) (Abstract, Annual Meeting American Phytopathological Society, Memphis, Tenn.: APS Press) reported on the ability of exogenously added fumonisins to accelerate disease development and increase sporulation of *Fusarium moniliform* and *F. oxysporum* on tomato.

Enzymes that degrade the fungal toxin fumonisin to the compound AP1 have been identified in U.S. Pat. No. 5,716, 820 and pending U.S. patent application Ser. Nos. 08/888, 949 and 08/888,950, both filed Jul. 7, 1997, and hereby incorporated by reference. Plants expressing a fumonisin esterase enzyme, infected by fumonisin producing fungus, and tested for fumonisin and AP1 were found to have low levels of fumonisin but high levels of AP1. AP1 is less toxic than fumonisin to plants and probably also animals, but contamination with AP1 is still a concern. The best result would be complete detoxification of fumonisin to a non-toxic form. Therefore enzymes capable of degrading AP1 are necessary for the further detoxification of fumonisin.

SUMMARY OF THE INVENTION

Compositions and methods for catabolism and detoxification of fumonisin and fumonisin-degradation products as well as fumonisin-related toxins are provided. In particular, proteins involved in catabolism and transmembrane transport of fumonisin and fumonisin catabolic products are provided. Nucleotide sequences corresponding to the proteins are also included. The compositions are useful in the detoxification and degradation of fumonisin. The nucleotide sequences can be used in expression cassettes for transformation of host cells of interest. The compositions and methods of the invention are steps in a catabolic pathway for fumonisin. Thus, organisms can be genetically modified to provide for the catabolism and detoxification of fumonisin and fumonisin-related toxins.

In particular, expression cassettes for expression of the enzymes in plants and other organisms are provided as well as transformed plants and other host cells.

DETAILED DESCRIPTION OF THE INVENTION

The catabolic pathway for detoxification and degradation of fumonisin is provided. Particularly, enzymes involved in the degradation of fumonisin from *Exophiala spinifera* (American Type Culture Collection Deposit No. 74269) and nucleotide sequences encoding such enzymes are disclosed. Such enzymes and nucleotide sequences find use in the breakdown of fumonisin and fumonisin-related toxins as well as degradation products thereof. In this regard, enzymes can be synthesized and utilized or, alternatively, organisms can be transformed with the DNA sequences of the invention and used to detoxify fumonisin.

Figure 1:
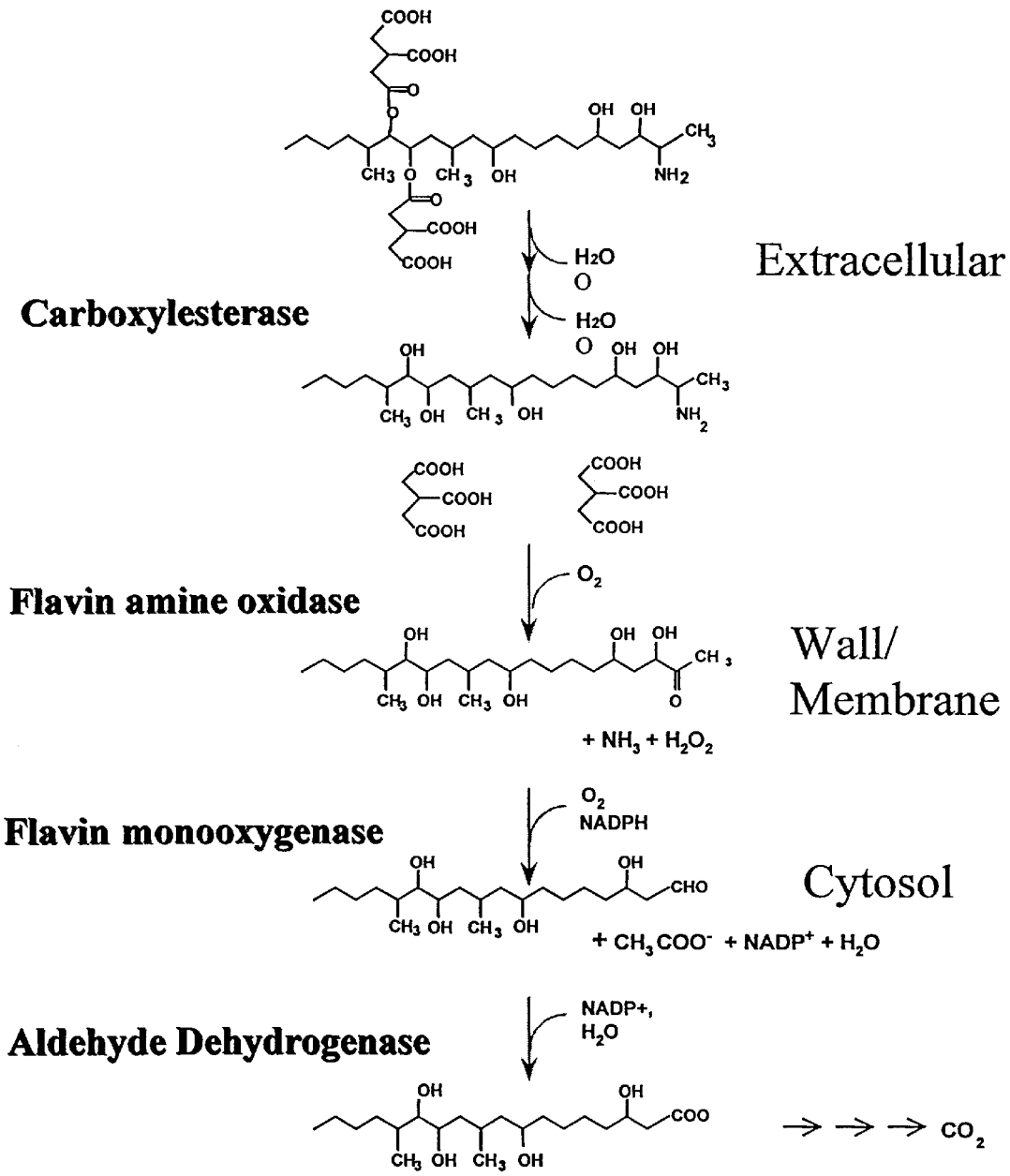
FIG. 1 sets forth the proposed pathway for fumonisin degradation by *Exophiala spinifera*.
Figure 2:
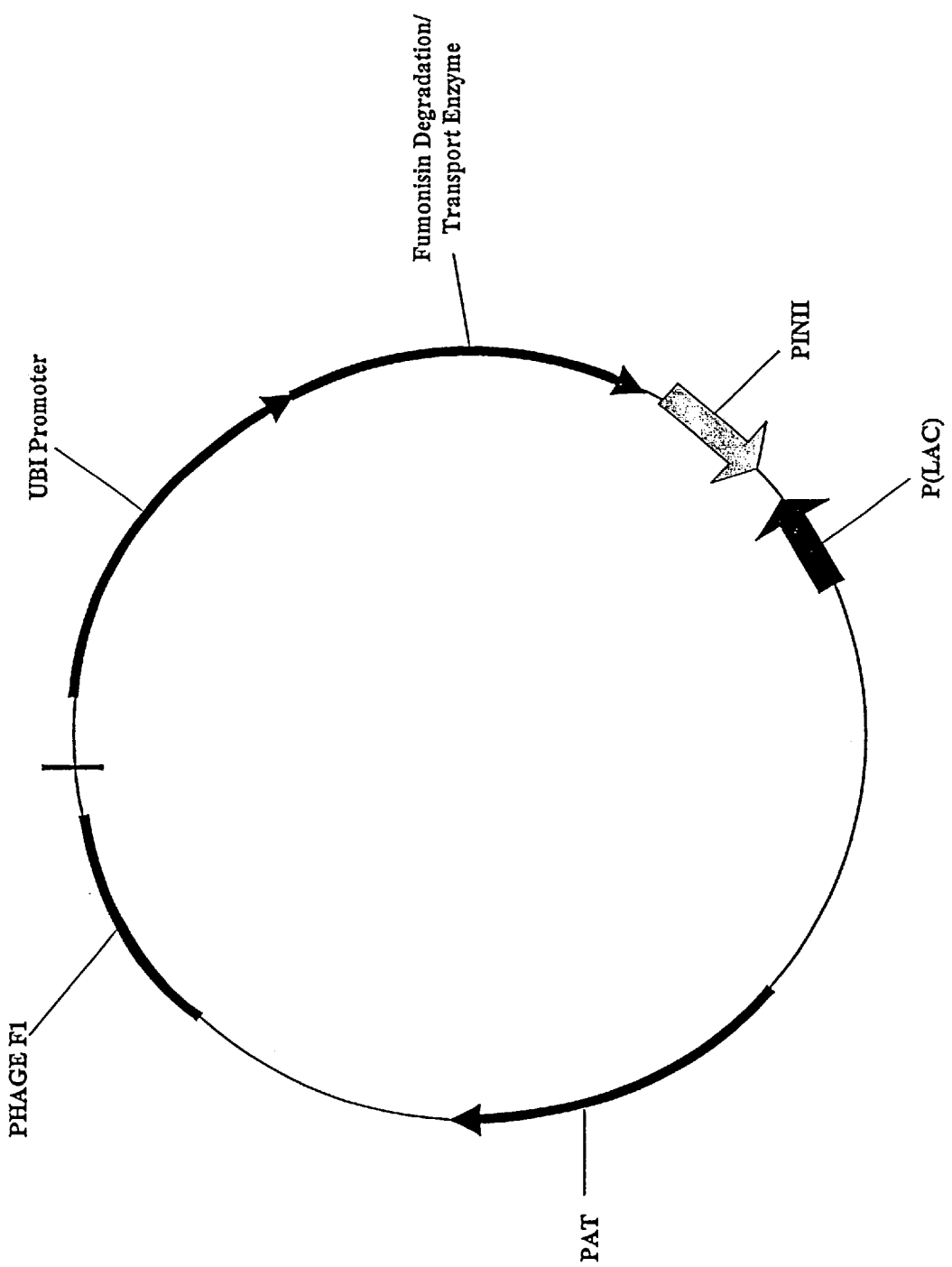
FIG. 2 schematically illustrates a plasmid vector comprising the gene for one of the fumonisin degradative enzymes of the invention operably linked to the ubiquitin promoter.

A proposed pathway for the degradation of fumonisin by *Exophiala spinifera* is provided in FIG. 1. The present invention encompasses enzymes and nucleotide sequences encoding the enzymes involved in this degradation pathway for fumonisin. Compositions of the invention include a flavin monooxygenase, an aldehyde dehydrogenase, a permease, and a p-glycoprotein that are involved in the fumonisin degradation pathway. In particular, the present invention provides for isolated nucleic acid molecules comprising nucleotide sequences encoding the amino acid sequences shown in SEQ ID NOS:3, 5, 8, and 11, or the nucleotide sequences encoding the DNA sequences obtained from the overlapping clones deposited in a bacterial host with the American Type Culture Collection and assigned Accession Number PTA-299. By "DNA sequence obtained from the overlapping clones" is intended that the DNA sequence of the fumonisin degrading enzymes can be obtained by sequencing the individual clones which together comprise the entire fumonisin degrading enzymes. Further provided are polypeptides having an amino acid sequence encoded by a nucleic acid molecule described herein, for example those set forth in SEQ ID NOS:1, 2, 4, 6, 7, 9 and 10, the DNA sequences obtained from the overlapping clones deposited in a bacterial host with the American Type Culture Collection and assigned Accession Number PTA-299, and fragments and variants thereof.

Ten plasmids containing overlapping clones were deposited with the American Type Culture Collection, Manassas, Va., and assigned Accession Number PTA-299. The plasmids designated as F_perm3.5 and F_perm4.4 contain common sequences at the regions were they overlap to form the nucleotide sequence encoding a permease. The plasmids designated as F_p-glyco1L4, F_p-glyco5.13, and F_p-glyco6.43 contain common sequences at the regions were they overlap to form the nucleotide sequence encoding a p-glycoprotein. And the plasmids designated F_Alde1.1, F_Alde2.2, and F_Alde2.5 contain common sequences at the regions were they overlap to form the nucleotide sequence of an aldehyde dehydrogenase. One of skill in the art by sequencing the clones and aligning the overlap may obtain the entire sequence of the permease, the p-glycoprotein, and the aldehyde dehydrogenase.

These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence degrade or catabolize fumonisn. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a fumonisin-degrading nucleotide sequence that encodes a biologically active portion of a fumonisin-degrading protein of the invention will encode at least 15, 25, 30, 50, 100, 150, 200, or 250, 300, 400, 500, 600, 700, 800, 900, 1,000, 1,100, 1,200 contiguous amino acids, or up to the total number of amino acids present in a full-length fumonisin-degrading protein of the invention (for example, 545, 487, 525, 1,263 amino acids for SEQ ID NOS:3, 5, 8 and 11, respectively). Fragments of a fumonisin-degrading nucleotide sequence that are useful as hybridization probes for PCR primers generally need not encode a biologically active portion of a fumonisin-degrading protein.

Thus, a fragment of a fumonisin-degrading nucleotide sequence may encode a biologically active portion of a fumonisin-degrading protein, or it may be a fragment that can be used as a hybridization probe or PCR primer using methods disclosed below. A biologically active portion of a fumonisin-degrading protein can be prepared by isolating a portion of one of the fumonisin-degrading nucleotide sequences of the invention, expressing the encoded portion of the fumonisin-degrading protein (e.g., by recombinant expression in vitro), and assessing the activity of the encoded portion of the fumonisin-degrading protein. Nucleic acid molecules that are fragments of a fumonisin-degrading nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400, 1500, 1, 600, 1,800, 2,000, 2,200, 2,400, 2,600, 2,800, 3,000, 3,200, 3,400, 3,600, 3,800, 3,900 nucleotides, or up to the number of nucleotides present in a full-length fumonisin-degrading nucleotide sequence disclosed herein (for example, 1,691, 1,638, 1,464, 1,764, 1,578, 3,999, 3,792 nucleotides for SEQ ID NOS:1, 2, 4, 6, 7, 9, and 10 respectively).

By "variants" is intended substantially similar sequences. For nucleotide sequences, conservative variants include those sequences that, because of the degeneracy of the genetic code, encode the amino acid sequence of one of the fumonisin-degrading polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a fumonisin-degrading protein of the invention. Generally, nucleotide sequence variants of the invention will have at least 40%, 50%, 60%, 70%, generally, 80%, preferably 85%, 90%, up to 95%, 98% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the fumonisin-degrading proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired ability to degrade or catabolize fumonisin. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by a decrease or loss in the toxic activity of fumonisin or AP1.

Variant nucleotide sequences and proteins also encompass sequences and proteins derived from a mutagenic and recombinogenic procedure such as DNA shuffling. With such a procedure, one or more different fumonisin-degrading coding sequences can be manipulated to create a new fumonisin-catabolizing possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the fumonisin-degrading genes of the invention and other known fumonisin-catabolizing genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The carboxylesterase and amine oxidase have been previously described in U.S. Pat. No. 5,716,820 and pending U.S. patent application Ser. Nos. 08/888,949 and 08/888,950. Such disclosures are herein incorporated by reference. Thus, the sequences of the invention can be used in combination with those previously disclosed or disclosed in co-pending application Ser. Nos. 09/352,168 and 09/352,159, entitled "Amino Polyolamine Oxidase Polynucleotides and Related Polypeptides and Methods of Use", herein incorporated by reference. The enzymes and nucleotide sequences of the present invention provide a means for continued catabolism of the fumonisin-degradation products obtained after degradation with at least the carboxylesterase and amine oxidase.

The practice of the present invention will employ, unless otherwise indicated, conventional techniques of botany, microbiology, tissue culture, molecular biology, chemistry, biochemistry, and recombinant DNA technology, which are within the skill of the art. Such techniques are explained fully in the literature. See, e.g., Langenheim and Thimann, (1982) *Botany: Plant Biology and Its Relation to Human Affairs* (John Wiley); Vasil, ed. (1984) *Cell Culture and Somatic Cell Genetics of Plants,* Vol. 1; Stanier et al. (1986) *The Microbial World* (5th ed., Prentice-Hall); Dhringra and Sinclair (1985) *Basic Plant Pathology Methods* (CRC Press); Maniatis et al. (1982) *Molecular Cloning: A Laboratory Manual* (Cold Spring Harbor Laboratory Press, Cold Spring Harbor, N.Y.); Glover, ed. (1985) *DNA Cloning,* Vols. I and II; Gait, ed. (1984) *Oligonucleotide Synthesis;* Hames and Higgins, eds. (1984) *Nucleic Acid Hybridization;* and the series *Methods in Enzymology* (Colowick and Kaplan, eds., Academic Press, Inc.).

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae, and protozoa, as well as other unicellular structures.

A "fumonisin-producing microbe" is any microbe capable of producing the mycotoxin fumonisin or analogues thereof. Such microbes are generally members of the fungal genus Fusarium, as well as recombinantly derived organisms that have been genetically altered to enable them to produce fumonisin or analogues thereof.

By "degrading or catabolizing fumonisin" is meant any modification to the fumonisin or AP1 molecule that causes a decrease or loss in its toxic activity. Such a change can comprise cleavage of any of the various bonds, oxidation, reduction, the addition or deletion of a chemical moiety, or any other change that affects the activity of the molecule. In a preferred embodiment, the modification includes hydrolysis of the ester linkage in the molecule as a first step and then oxidative deamination. Furthermore, chemically altered fumonisin can be isolated from cultures of microbes that produce an enzyme of this invention, such as by growing the organisms on media containing radioactively-labeled fumonisin, tracing the label, and isolating the degraded toxin for further study. The degraded fumonisin can be compared to the active compound for its phytotoxicity or mammalian toxicity in known sensitive species, such as porcines and equines. Such toxicity assays are known in the art. For example, in plants a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies, e.g., using cell suspension cultures.

For purposes of the invention, the fumonisin or fumonisin degradation products will be degraded to at least about 50% to about 10% or less of the original toxicity, preferably about 30% to about 5% or less, more preferably about 20% to about 1% or less.

By "fumonisin esterase" is meant any enzyme capable of hydrolysis of the ester linkage in fumonisin. Two examples of such enzymes are ESP1 and BEST1 found in U.S. Pat. No. 5,716,820 and pending U.S. application Ser. Nos. 08/888,949 and 08/888,950, both filed Jul. 7, 1997.

By "structurally related mycotoxin" is meant any mycotoxin having a chemical structure related to a fumonisin such as fumonisin B1, for example AAL toxin, fumonisin B2, fumonisin B3, fumonisin B4, fumonisin C1, fumonisin A1 and A2, and their analogues, as well as other mycotoxins having similar chemical structures that would be expected to be detoxified by activity of the fumonisin degradative enzymes elaborated by *Exophiala spinifera,* American Type Culture Collection Accession No. 74269, *Rhinocladiella atrovirens,* American Type Culture Collection Accession No. 74270, or the bacterium of American Type Culture Collection Accession No. 55552.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Persing et al., ed. (1993) *Diagnostic Molecular Microbiology: Principles and Applications* (American Society for Microbiology, Washington, D.C.). The product of amplification is termed an amplicon.

By "host cell" is meant a cell that contains a vector and supports the replication and/or expression of the expression vector. Host cells may be prokaryotic cells such as *E. coli,* or eukaryotic cells such as yeast, insect, amphibian, or mammalian cells. Preferably, host cells are monocotyledonous or dicotyledonous plant cells, including but not limited to maize, sorghum, sunflower, soybean, wheat, alfalfa, rice, cotton, and tomato. A particularly preferred monocotyledonous host cell is a maize host cell.

The term "hybridization complex" includes reference to a duplex nucleic acid structure formed by two single-stranded nucleic acid sequences selectively hybridized with each other.

As used herein, "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, or analogues thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including inter alia, simple and complex cells.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria that comprise genes expressed in plant cells, such as Agrobacterium or Rhizobium. Examples are promoters that preferentially initiate transcription in certain tissues, such as leaves, roots, seeds, fibers, xylem vessels, tracheids, or sclerenchyma. Such promoters are referred to as "tissue preferred". A "cell type" specific promoter primarily drives expression in certain cell types in one or more organs, for example, vascular cells in roots or leaves. An "inducible" promoter is a promoter that is under environmental control.

Examples of environmental conditions that may effect transcription by inducible promoters include anaerobic conditions or the presence of light. Another type of promoter is a developmentally regulated promoter. For example, a promoter that drives expression during pollen development. Tissue-preferred, cell type specific, developmentally regulated, and inducible promoters constitute the class of "non-constitutive" promoters. A "constitutive" promoter is a promoter that is active under most environmental conditions. Constitutive promoters are known in the art and include, for example, 35S promoter (Meyer et al. (1997) *J. Gen. Virol.* 78:3147–3151); ubiquitin; as well as those disclosed in U.S. Pat. Nos. 5,608,149; 5,608,144; 5,604,121; 5,569,597; 5,466,785; 5,399,680; 5,268,463; 5,608,142.

As used herein, "recombinant" includes reference to a cell or vector that has been modified by the introduction of a heterologous nucleic acid or that the cell is derived from a cell so modified. Thus, for example, recombinant cells express genes that are not found in identical form within the native (nonrecombinant) form of the cell or express native genes that are otherwise abnormally expressed, underexpressed, or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The nucleotide sequences of the invention can be used to isolate corresponding sequences from other organisms. In this manner, methods such as PCR, hybridization, and the like can be used to identify such sequences based on their sequence homology to the sequences set forth herein. Sequences isolated based on their sequence identity to the entire fumonisin-degrading sequences set forth herein or to fragments thereof are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the fumonisin-degrading sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire fumonisin-degrading sequences disclosed herein, or one or more portions thereof, may be used as a probe capable of specifically hybridizing to corresponding fumonisin-degrading sequences and messenger RNAs. To achieve specific hybridization under a variety of conditions, such probes include sequences that are unique among fumonisin-degrading sequences and are preferably at least about 10 nucleotides in length, and most preferably at least about 20 nucleotides in length. Such probes may be used to amplify corresponding fumonisin-degrading sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.$+16.6$ (log M)$+0.41$ (%GC)$-0.61$ (% form)$-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with $\geq 90\%$ identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, New York); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that encode for a fumonisin-degradative protein and hybridize to the fumonisin-degrading sequences disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length CDNA or gene sequence, or the complete CDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignments are performed using the default parameters of the above mentioned programs. Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a fill mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

As indicated, the enzymes and nucleotide sequences encoding such enzymes are involved in the degradation of fumonisin and fumonisin-like compounds. Such enzymes and nucleotide sequences can be utilized alone or in combination to engineer microbes or other organisms to metabolize fumonisin and resist its toxic effects.

Fumonisin is produced in the intercellular spaces (apoplast) of Fusarium-infected maize cells. Thus, the apoplast is the preferred location for esterase and deaminase, flavin amine oxidase and possibly other catabolic enzymes. It is possible that some fumonisin could diffuse or be transported into the maize cells before it is broken down by the apoplastic enzymes and may escape catabolism. Thus, it may be beneficial to express a fumonisin pump and reroute the fumonisin or degradation products in such cells. In this manner, any fumonisin entering the cell will be pumped out and reexposed to catabolic enzymes. Similar toxin pumps exist in other toxin-producing fungi that show resistance to toxins or antibiotics. Such a pump useful in the invention and disclosed herein is a P-glycoprotein homolog.

More complete catabolism of fumonisin in transgenic organisms may be provided by esterase and deaminase enzymes. Exophiala enzymes that can further oxidize fumonisin breakdown-products are not detected extracellularly. Such enzymes in all likelihood exist in the cytoplasm, where adequate cofactors such as $NAD^+$ or NADP are found. The fumonisin-induced metabolite transporter is predicted to provide transport of degradation products into cells where they can be further broken down by other enzymes. In this manner, a permease enzyme may be utilized in a heterologous system to transport either AP1 precursors or fumonisin degradation products into the cytoplasm.

The monooxygenase is expected to result in the oxidation of 2-OP to a compound that lacks a keto group, having instead a terminal aldehyde group, or possibly a carboxylate group. See, for example, Trudgill et al. (1984) in *Microbial Degradation of Organic Compounds*, ed. Gibson (Microbiology Series Vol. 13, Marcel Dekker, New York), Chapter 6; and Davey and Trudgill (1977) *Eur. J. Biochem.* 74:115.

This reaction is due to a type of enzymatic oxidation referred to as Baeyer-Villiger oxidation, in which monooxygen is inserted adjacent to a keto function, resulting in a lactone or ester linkage. The metabolism of trans-cyclohexane-1,2 diol by Acinetobacter provides a model for the activity of a Baeyer-Villiger monooxygenase on 2-OP. This diol is first oxidized to ortho hydroxy cyclohexanone and then a monooxygen is inserted between the quinone and hydroxy functions by the Baeyer-Villiger enzyme, cyclohexanone monooxygenase. This intermediate spontaneously rearranges to a linear aldehyde carboxylic acid. By analogy, for 2-OP it is predicted oxygen is inserted between carbons 2 and 3 followed by spontaneous cleavage to a C22 aldehyde and acetic acid. Further oxidation by an aldehyde dehydrogenase would convert this compound to a carboxylic acid; other catabolic products would also be possible given the high reactivity of the aldehyde group. Additional steps include the use of an aldehyde dehydrogenase to result in the oxidation of the aldehyde product of fumonisin to a hydroxy carboxylic acid.

It is recognized that the DNA sequences of the invention can be inserted into expression cassettes and used to transform a variety of organisms. Enzymes produced recombinantly may be tested for their ability to modify fumonisin or a fumonisin byproduct using labeled starting material and appropriate buffer and cofactor conditions. For example, to test aldehyde dehydrogenase activity, the aldehyde dehydrogenase produced in a recombinant manner would be incubated with cofactors, NAD+ or NADP, and $^{14}$C-labeled 2-OP for various times and then an aliquot of the reaction mix spotted on TLC. Enzyme activity would be indicated by the appearance of a new radiolabeled spot at a different Rf on the TLC plate.

The sequences of the invention can be introduced into any host organism. The sequences to be introduced may be used in expression cassettes for expression in the host of interest where expression in the host is necessary for transcription.

Where expression cassettes are needed, such expression cassettes will comprise a transcriptional initiation region linked to the coding sequence or antisense sequence of the nucleotide of interest. Such an expression cassette is provided with a plurality of restriction sites for insertion of the sequence to be under the transcriptional regulation of the regulatory regions. The expression cassette may additionally contain selectable marker genes.

The marker gene confers a selectable phenotype on the transformed cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance ; the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

The transcriptional initiation region, the promoter, may be native or analogous or foreign or heterologous to the host as well as to the coding sequence. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-to-3' direction of transcription, a transcriptional and translational initiation region, a DNA sequence of interest, and a transcriptional and translational termination region functional in the host. The termination region may be native with the transcriptional initiation region, may be native with the DNA sequence of interest, or may be derived from another source. For use in plants or plant cells, convenient termination regions are available from the Ti-plasmid of *A. tumefaciens,* such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acids Res.* 15:9627–9639.

Nucleotide sequences of the invention are provided in expression cassettes for expression in the host cell of interest. The cassette will include 5' and 3' regulatory sequences operably linked to the sequence of interest. The cassette may additionally contain at least one additional sequence to be cotransformed into the organism. Alternatively, the additional sequence(s) can be provided on another expression cassette.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA,* ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In the same manner, a plant can be transformed with the nucleotide sequences of the invention to provide complete detoxification of fumonisin in the transformed plant and plant products. Such plants include, for example, species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Caco, and Populus.

As used herein, “transgenic plant” includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, nonrecombinant viral infection, nonrecombinant bacterial transformation, nonrecombinant transposition, or spontaneous mutation.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The degradative enzymes can be fermented in a bacterial host and the resulting bacteria processed and used as a microbial spray. Any suitable microorganism can be used for this purpose. See, for example, Gaertner et al. (1993) in *Advanced Engineered Pesticides*, Kim (Ed.).

The genes of the invention can be introduced into microorganisms that multiply on plants (epiphytes) to deliver enzymes to potential target crops. Epiphytes can be gram-positive or gram-negative bacteria, for example.

The microorganisms that have been genetically altered to contain at least one degradative gene and protein may be used for protecting agricultural crops and products. In one aspect of the invention, whole, i.e., unlysed, cells of the transformed organism are treated with reagents that prolong the activity of the enzyme produced in the cell when the cell is applied to the environment of a target plant. A secretion signal sequence may be used in combination with the gene of interest such that the resulting enzyme is secreted outside the host cell for presentation to the target plant.

Plant signal sequences, including, but not limited to, signal-peptide encoding DNA/RNA sequences which target proteins to the extracellular matrix of the plant cell (Dratewka-Kos et al., (1989) *J. Biol. Chem.* 264:4896–4900), the *Nicotiana plumbaginifolia* extension gene (DeLoose, et al. (1991) *Gene* 99:95–100), signal peptides which target proteins to the vacuole like the sweet potato sporamin gene (Matsuka et al. (1991) *PNAS* 88:834) and the barley lectin gene (Wilkins et al. (1990) *Plant Cell* 2:301–313), signal peptides which cause proteins to be secreted such as that of PRIb (Lind et al. (1992) *Plant Mol. Biol.* 18:47–53), or the barley alpha amylase (BAA) (Rahmatullah et al. (1989) *Plant Mol. Biol.* 12:119) and hereby incorporated by reference, or from the present invention the signal peptide from the ESP1 or BEST1 gene, or signal peptides which target proteins to the plastids such as that of rapeseed enoyl-Acp reductase (Verwaert et al. (1994) *Plant Mol. Biol.* 26:189–202) are useful in the invention.

In this manner, at least one of the genes encoding a degradation enzyme of the invention may be introduced via a suitable vector into a microbial host, and said transformed host applied to the environment or plants or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the polypeptide pesticide, and, desirably, to provide for improved protection of the enzymes of the invention from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Pichia, Cryptococcus, Kluyveromyces, Sporobolomyces, Rhodotorula, and Aureobasidium. Of particular interest are such phytosphere bacterial species as

*Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pullulans.*

Illustrative prokaryotes, both Gram-negative and -positive, include Enterobacteriaceae, such as Escherichia, Erwinia, Shigella, Salmonella, and Proteus; Bacillaceae; Rhizobiaceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae; and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Other considerations include ease of formulation and handling, economics, storage stability, and the like.

A number of ways are available for introducing a gene expressing the degradation enzyme into the microorganism host under conditions that allow for stable maintenance and expression of the gene. For example, expression cassettes can be constructed that include the DNA constructs of interest operably linked with the transcriptional and translational regulatory signals for expression of the DNA constructs, and a DNA sequence homologous with a sequence in the host organism, whereby integration will occur, and/or a replication system that is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. supra; Maniatis et al., eds. (1982) *Molecular Cloning: A Laboratory Manual* (Cold Spring Harbor Laboratory, Cold Spring Harbor, N.Y.); Davis et al., eds. (1980) *Advanced Bacterial Genetics* (Cold Spring Harbor Laboratory, Cold Spring Harbor, N.Y.); and the references cited therein.

It is recognized that the construction of a catabolic pathway in a transformed organism is a complicated feat. Therefore, any means for assembling the enzymes of interest into an organism of interest is encompassed. For example, a single nucleotide sequence encoding all of the desired enzymes or multiples thereof may be transformed into the host organism. When microorganisms are to be applied to the environment or to a plant, several microorganisms, each transformed with one, two, three, or more nucleotide sequences of the invention, may be utilized. In this manner, all of the enzymes necessary to bring about detoxification of fumonisin and related products may be presented to the environment or to the plant by applying a mixture of transformed organisms or a single organism capable of expressing the entire pathway or at least expressing enough of the pathway to detoxify fumonisin.

In plants, nucleotide sequences for an enzyme may be transformed into a plant and crossed with plants expressing a different enzyme. In this manner, progeny can be obtained having the entire sequence or enough of the sequence to detoxify fumonisin. Alternatively, a plant can be transformed with nucleotides encoding several enzymes at the same time. In some tissue culture systems it is possible to transform callus with one nucleotide sequence, establish a stable culture line, and then transform the callus a second time with a second nucleotide sequence. The process may be repeated to introduce additional sequences.

To facilitate the expression of more than one enzyme in a cell, e.g. a plant cell, fusion proteins may be created. Generally, a spacer region is included between the proteins. The spacer region may comprise a cleavage site for cleavage by an endogenous or introduced protease.

The present invention also relates to a method of detoxifying a fumonisin or a structurally related mycotoxin with the enzymes from *Exophiala spinifera* (American Type Culture Collection Accession No. 74269), during the processing of grain for animal or human food consumption, during the processing of plant material for silage, or in food crops contaminated with a toxin-producing microbe, such as but not limited to, tomato. Since the atmospheric ammoniation of corn has proven to be an ineffective method of detoxification (see Haumann (1995) *INFORM* 6:248–257), such a methodology during processing is particularly critical where transgenic detoxification is not applicable.

In this embodiment, the fumonisin degradative enzymes found in *Exophiala spinifera* (American Type Culture Collection Accession No. 74269), are presented to grain, plant material for silage, or a contaminated food crop, or during the processing procedure, at the appropriate stages of the procedure and in amounts effective for detoxification of fumonisins and structurally related mycotoxins. Detoxification by this method can occur not only during the processing, but also any time prior to or during the feeding of the grain or plant material to an animal or incorporation of the grain or food crop into a human food product, or before or during ingestion of the food crop. The enzymes or microorganisms can be introduced during processing in appropriate manners, for example, as a wash or spray, or in dried or lyophilized form or powered form, depending upon the nature of the milling process and/or the stage of processing at which the enzymatic treatment is carried out. See generally, Hoseney, R.C. (1990) *Principles of Cereal Science and Technology,* American Assn. of Cereal Chemists, Inc. (especially Chapters 5, 6 and 7); Jones, J. M. (1992) *Food Safety,* Eagan Press, St. Paul, Minn. (especially Chapters 7 and 9); and Jelen, P. (1985) *Introduction to Food Processing,* Restan Publ. Co., Reston, Va. Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The esterase from *Exophiala spinifera* (American Type Culture Collection Accession No. 74269), showed a range of activity from about pH 3 to about pH 6, and the esterase from the bacterium of the American Type Culture Collection Accession No. 55552 showed a range of activity from about pH 6 to about pH 9 (U.S. Pat. No. 5,716,820, supra). The APAO enzyme from *Exophiala spinifera* (American Type Culture Collection Accession No. 74269) has a pH range of activity from pH 6 to pH 9.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides, or mixtures of several of these preparations, if desired, together with further agriculturally acceptable carriers, surfactants, or application-promoting adjuvants customarily employed in the art of formulation. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers.

The enzymes can be introduced during processing in appropriate manners, for example as a wash or spray, or in dried or lyophilized form or powered form, depending upon the nature of the milling process and/or the stage of processing at which the enzymatic treatment is carried out. See generally, Hoseney (1990) *Principles of Cereal Science and Technology* (American Association of Cereal Chemists, Inc.), especially Chapters 5, 6, and 7; Jones (1992) Food Safety (Eagan Press, St. Paul, Minn.), especially Chapters 7 and 9; and Jelen (1985) *Introduction to Food Processing* (Restan Publishing Company, Reston, Va.). Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The enzymes from *Exophiala spinifera*, American Type Culture Collection Accession No. 74269, showed a range of activity for esterase from about pH 3 to about pH 7 (U.S. Pat. No. 5,716,820, supra). The APAO enzyme from *Exophiala spinifera*, American Type Culture Collection Accession No. 74269, has a pH range of activity from pH 6 to pH 9.

In another embodiment, ruminal microorganisms can be genetically engineered to contain and express at least one of the fumonisin degradation enzymes of the invention. The genetic engineering of microorganisms is now an art-recognized technique, and ruminal microorganisms so engineered can be added to feed in any art-recognized manner, for example as a probiotic or inoculant. In addition, microorganisms, plants, or other organisms or their cultured cells in vitro capable of functioning as bioreactors can be engineered so as to be capable of mass producing the degradative enzymes of *Exophiala spinifera* (American Type Culture Collection Accession No. 74269).

Another embodiment of the present invention is the use of the enzymes of the present invention as detection reagents for fumonisins and related compounds. The enzymes of the present invention can be used as detection reagents because of the high specificity of the esterase and deaminase enzymes, and the fact that hydrolysis followed by amine oxidation can be monitored by detection of hydrogen peroxide or ammonia using standard reagents (analogous to a glucose detection assay using glucose oxidase). Hydrogen peroxide is often measured by linking a hydrogen peroxide-dependent peroxidase reaction to a colored or otherwise detectable peroxidase product (e.g., Demmano et al. (1996) *European Journal of Biochemistry* 238(3):785–789). Ammonia can be measured using ion-specific electrodes: Fritsche et al. (1991) *Analytica Chimica Acta* 244(2):179–182; West et al. (1992) *Analytical Chemistry* 64(5):533–540, and all herein incorporated by reference) or by GC or other chromatographic method.

For example, recombinant or non-recombinant, active fumonisin esterase, APAO, and proteins of the invention are added in catalytic amounts to a sample tube containing an unknown amount of fumonisins (FB1, FB2, FB3, FB4, or partial or complete hydrolysis products of these). The tube is incubated under pH and temperature conditions sufficient to convert any fumonisin in the sample to AP1, the AP1 to 2-OP, ammonia, and hydrogen peroxide, and to further degradation products. Then suitable reagents are added for quantification of the hydrogen peroxide or ammonia that were generated stoichiometrically from fumonisins. By comparison with control tubes that received no esterase or APAO enzyme, the amount of fumonisin present can be calculated in direct molar proportion to the hydrogen peroxide or ammonia detected, relative to a standard curve.

This invention can be better understood by reference to the following nonlimiting examples. It will be appreciated by those skilled in the art that other embodiments of the invention may be practiced without departing from the spirit and the scope of the invention as herein disclosed and claimed.

Experimental

EXAMPLE 1

Fungal and Bacterial Isolates

Exophiala isolates from maize were isolated as described in U.S. Pat. No. 5,716,820 and pending U.S. application Ser. Nos. 08/888,949 and 08/888,950, both filed Jul. 7, 1997, and herein incorporated by reference.

Isolation Methods

Direct isolation of black yeasts from seed was accomplished by plating 100 microliters of seed wash fluid onto YPD or Sabouraud agar augmented with cycloheximide (500 mg/liter) and chloramphenicol (50 mg/liter). Plates were incubated at room temperature for 7–14 days, and individual pigmented colonies that arose were counted and cultured for analysis of fumonisin-degrading ability as described above.

Analysis of Fumonisins and Metabolism Products

Analytical thin-layer chromatography was carried out on 100% silanized $C_{18}$ silica plates (Sigma #T-7020; 10×10 cm; 0.1 mm thick) by a modification of the published method of Rottinghaus (Rottinghaus et al. (1992) *J. Vet. Diagn. Invest.* 4:326, and herein incorporated by reference).

To analyze fumonisin esterase activity, sample lanes were pre-wet with methanol to facilitate sample application. After application of from 0.1 to 2 µl of aqueous sample, the plates were air-dried and developed in MeOH:4% KCl (3:2) or MeOH:0.2 M KOH (3:2) and then sprayed successively with 0.1 M sodium borate (pH 9.5) and fluorescence (0.4 mg/ml in acetonitrile). Plates were air-dried and viewed under long-wave UV.

For analysis of APAO activity, an alternative method was used. Equal volumes of sample and $^{14}C$-AP1 (1 mg/ml, pH 8) substrate were incubated at room temperature for six days. Analytical thin-layer chromatography was then carried out on C60 HPK silica gel plates (Whatman #4807-700; 10×10 cm; 0.2 mm thick). After application of from 0.1 to 2 µl of aqueous sample, the plates were air dried and developed in $CHCl_3$:MeOH:$CH_3COOH$:$H_2O$ (55:36:8:1). Plates were then air dried and exposed to PhosphorImager screen or autoradiographic film. A Storm PhosphorImager was used to scan the image produced on the screen.

Alkaline Hydrolysis of FB1 to AP1

FB1 or crude fumonisin $C_8$ material was suspended in water at 10–100 mg/ml and added to an equal volume of 4 N NaOH in a screw-cap tube. The tube was sealed and incubated at 60° C. for 1 hr. The hydrolysate was cooled to room temperature and mixed with an equal volume of ethyl acetate, centrifuged at 1000 RCF for 5 minute and the organic (upper) layer recovered. The pooled ethyl acetate layers from two successive extractions were dried under $N_2$ and resuspended in distilled $H_2O$. The resulting material (the aminopentol of FB1 or "AP1") was analyzed by TLC.

Enzyme Activity of Culture Filtrate and Mycelium

*Exophiala spinifera* isolate 2141.10 was grown on YPD agar for 1 week, and conidia were harvested, suspended in sterile water, and used at 105 conidia per ml to inoculate sterile Fries mineral salts medium containing 1 mg/ml purified FB1 (Sigma Chemical Co.). After 2 weeks incubation at 28° C. in the dark, cultures were filtered through 0.45 micron cellulose acetate filters and rinsed with Fries mineral salts. Fungal mycelium was suspended in 15 mL of 0.1% FB1, pH 5.2+1 mM EDTA+3 µg/mL Pepstatin A+1.5 µg/mL Leupeptin and disrupted in a Bead Beater™ using 0.1 mm beads and one minute pulses, with ice cooling. Hyphal pieces were collected by filtering through Spin X™ (0.22 µm), and both mycelial supernatant and original culture filtrates were assayed for fumonisin modification by methods outlined above.

Preparation of Crude Culture Filtrate

Agar cultures grown as above were used to inoculate YPD broth cultures (500 ml) in conical flasks at a final concentration of 105 conidia per ml culture. Cultures were incubated 5 days at 28° C. without agitation and mycelia harvested by filtration through 0.45 micron filters under vacuum. The filtrate was discarded, and the mycelial mat was washed and resuspended in sterile carbon-free, mineral salts medium (1 g/liter $NH_3NO_4$; 1 g/liter $NaH_2PO_4$; 0.5 g/liter $MgCl_2$; 0.1 g/liter NaCl; 0.13 g/liter $CaCl_2$; 0.02 g/liter $FeSO_4.7H_2O$, pH 4.5) containing 0.5 mg/ml alkaline hydrolyzed crude FB1. After 3–5 days at 28° C. in the dark with no agitation the cultures were filtered through low protein binding 0.45 micron filters to recover the culture filtrate. Phenylmethyl sulfonyl fluoride (PMSF) was added to a concentration of 2.5 mM and the culture filtrate was concentrated using an Amicon™ YM10 membrane in a stirred cell at room temperature and resuspended in 50 mM sodium acetate, pH 5.2 containing 10 mM $CaCl_2$. The crude culture filtrate (approx. 200-fold concentrated) was stored at −20° C.

To obtain preparative amounts of enzyme-hydrolyzed fumonisin, 10 mg of FB1 (Sigma) was dissolved in 20 mL of 50 mM sodium acetate at pH 5.2+10 mM $CaCl_2$, and 0.25 mL of 200× concentrated crude culture filtrate of 2141.10 was added. The solution was incubated at 37° C. for 14 hours, and then cooled to room temperature. The reaction mixture was brought to approximately pH 9.5 by addition of 0.4 mL of 4 N KOH, and the mixture was extracted twice with 10 mL ethyl acetate. The combined organic layers were dried under $LN_2$ and resuspended in $dH_2O$. 2.5 milligrams of organic extracted material were analyzed by Fast Atom Bombardment (FAB) mass spectrometry. The resulting mass spectrum showed a major ion at M/z (+1)=406 mass units, indicating the major product of enzymatic hydrolysis was AP1, which has a calculated molecular weight of 405.

EXAMPLE 2

Preparation of AP1-induced and Non-induced Mycelium

Liquid cultures of *Exophiala spinifera* isolate 2141.10 were prepared from YPD agar plates (Yeast Extract 10 gm, Bacto-Peptone 20 gm, Dextrose 0.5 gm, Bacto-Agar 15 gm per liter of water). Aliquots (400–500 uL) of a water suspension of *E. spinifera* cells from YPD agar were spread uniformly onto 150×15 mm YPD agar plates with 4 mm sterile glass beads. The plates were incubated at room temperature for 6–7 days. The mycelia/conidia were transferred from the agar plates into Mineral Salts Medium (MSM) ($Na_2HPO_4.7H_2O$ 0.2 gm, $NH_4Cl$ 1.0 gm, $CaCl_2.2H_2O$ 0.01 gm, $FeSO_4.7H_2O$ 0.02 gm per liter of distilled water, pH 4.5) and centrifuged at 5000×g, 4° C., 20 minutes to pellet the cells. The cell pellet was rinsed once in 40 mL MSM and recentrifuged. The rinsed cell pellet was used to inoculate MSM at a 1:19 ratio of packed cells:MSM. The culture was supplemented with AP1 to a final concentration of 0.5–1.0 mg/ml and incubated at 28° C., 100 rpm, in the dark to induce catabolic enzymes. The supernatants were removed by filtration through 0.45 cellulose acetate. The remaining mycelial mat was washed with sterile MSM and then frozen in liquid nitrogen for storage.

EXAMPLE 3

Effect of FB1 and AP1 on Maize Coleoptiles

Maize coleoptiles from 4 day dark-grown germinated maize seeds were excised above the growing point and placed in 96-well microliter plates in the presence of 60 microliters of sterile distilled water containing FB1 or AP1 at approximately equimolar concentrations of 1.5, 0.5, 0.15, 0.05, 0.015, 0.005, 0.0015, or 0.0005 millimolar, along with water controls. After 2 days in the dark at 28° C. the coleoptiles were placed in the light and incubated another 3 days. Injury or lack thereof was evaluated as follows:

|  | 0 | .0005 | .0015 | .005 | .015 | .05 | .15 | .5 | 1.5 | mM |
|---|---|---|---|---|---|---|---|---|---|---|
| FB1 | − | − | − | − | +/− | + | + | + | + | |
| AP1 | − | − | − | − | − | − | − | − | + | |

+ = brown necrotic discoloration of coleoptile
− = no symptoms (same as water control)

The results (see table above) indicate there is at least a 30-fold difference in toxicity between FB1 and AP1 to maize coleoptiles of this genotype. This is in general agreement with other studies where the toxicity of the two compounds was compared for plant tissues. In Lemna tissues, AP1 was approximately 40-fold less toxic (Vesonder et al. (1992) *Arch. Environ. Contam. Toxicol.* 23:464–467 (1992)). Studies with both AAL toxin and FB1 in tomato also indicate the hydrolyzed version of the molecule is much less toxic (Gilchrist et al. (1992) *Mycopathologia* 117: 57–64). Lamprecht et al. also observed an approximate 100-fold reduction in toxicity to tomato by AP1 versus FB1 (Lamprecht et al. (1994) *Phytopathology* 84:383–391).

EXAMPLE 4

Effect of FB1 and AP1 on Maize Tissue Cultured Cells (Black Mexican Sweet, BMS)

FB1 or AP1 at various concentrations was added to suspensions of BMS cells growing in liquid culture medium in 96-well polystyrene plates. After 1 week the cell density in wells was observed under low power magnification and growth of toxin-treated wells was compared to control wells that received water. Growth of BMS cells was significantly inhibited at 0.4 micromolar FB1, but no inhibition was observed until 40 micromolar AP1. This represents an approximate 100-fold difference in toxicity to maize tissue-cultured cells. Similarly Van Asch et al. observed significant inhibition of maize callus grown on solid medium at 1.4 micromolar FB1 (Van Asch et al. (1992) *Phytopathology* 82:1330–1332). AP1 was not tested in that study, however.

EXAMPLE 5

The polynucleotides were identified using a proprietary transcript imaging method that compares transcript patterns in two samples and allows cloning of differentially expressed fragments. This technology was developed by CuraGen® (New Haven, Conn.) (see Published PCT Patent Application No. WO 97/15690, published May 1, 1997, and hereby incorporated by reference). Fluorescently-tagged, PCR amplified cDNA fragments representing expressed transcripts can be visualized as bands or peaks on a gel tracing, and the cDNA from differentially expressed (induced or suppressed) bands can be recovered from a duplicate gel, cloned, and sequenced. Known cDNAs can be identified without the need for cloning, by matching the predicted size and partially known sequence of specific bands on the tracing.

Two RNA samples were obtained from cultures of *E. spinifera* grown for a specified period in a mineral salts medium containing either AP1 (induced condition) or gamma-aminobutyric acid (ABA; non-induced condition) as a sole carbon source. In the induced condition, fumonisin esterase, amine oxidase, enzyme activities are detected, whereas in the non-induced condition these activities are not detected. The methods used for induction of and detection of enzyme activity are described earlier (see Example 2 and Example 5). RNA was extracted from induced mycelium by Tri-Reagent methods (Molecular Research Center Inc., Cincinnati, Ohio) only using frozen tissue samples ground with a mortar and pestle 2-fold and up to 79-fold and greater until slushy and adding an additional extraction after the phase separation by extracting the aqueous phase one time with phenol, and two times with a phenol:chloroform:isoamyl alcohol mixture. The RNAs were submitted for CuraGen® transcript imaging to detect cDNA fragments that are induced specifically in the presence AP1. In the resulting gel tracing several bands were found which showed induction of at least 10-fold in AP1-grown cells as compared to cells grown in ABA. One set of induced fragments can be matched to the fumonisin esterase cDNA. The cloned bands and possible functions are provided in Table 2. Highly induced bands and their likely function are provided in Tables 2 and 3.

TABLE 2

| Clone ID | Best BLAST Hit | BLAST Hit Name, source, size | Prob | from-to | Function |
|---|---|---|---|---|---|
| | | Monooxygenase | | | |
| M1a0-388 | A28550 | cyclohexanone monooxygenase, Acinetobacter (flavin monooxygenase or FMO)EC 1.14.13.22 Length = 543 | 1.4e – 22 | 339–414 | Baeyer-Villiger oxidation of 2-OP1 (AP1-N1), utilizing molecular oxygen and reduced NADPH Or NADH |
| | | Aldehyde dehydrogenase (EC 1.) | | | |
| k0n0-235 passed | Y09876 | Aldehyde dehydrogenase (Nicotiana tabacum); Length = 542 | 1.1e – 07 | 152–191 | Oxidation of aldehyde product of FMO to carboxylic acid |
| | | Permease | | | |
| r0v0-239 | S64084 | Choline transport protein, yeast Length = 563 | 9.3e – 0.5 | 337–397 | Transport of 2-OP1 into the cytoplasm |
| r0w0-424 w0h0-268 | S51169 | amino acid transporter AAP4-Arabidopsis thalina len = 466 | 0.98 | 8–76 | Transport of 2-OP1 into the cytoplasm |
| r0w0-205 p0t0-308 (contig) | P53744 | KAPA/DAPA permease, yeast BIO5 Length = 561 | 2.1e – 07 | 446–488 | Transport of 2-OP1 into the cytoplasm |
| | | Transmembrane pump (P-glycoprotein homolog) | | | |
| r0g1-420 | S20548 | Leptomycin resistance protein, pmd1, Schizosaccharomyces pombe. Length = 1362 | 1.8e – 37 | 1255–1359 or 564–668 | Transmembrane pump that removes FB1 from the cytoplasm as a means of protection against its toxic activity |

TABLE 2-continued

| Clone ID | Best BLAST Hit | BLAST Hit Name, source, size | Prob | from-to | Function |
|---|---|---|---|---|---|
| g0s0-142 | | Leptomycin resistance protein, pmd1, Schizosaccharomyces pombe. Length = 1362 | | 527–588 | Transmembrane pump that removes FB1 from the cytoplasm as a means of protection against its toxic activity |
| l0c0-129 | | Leptomycin resistance protein, pmd1, Schizosaccharomyces pombe. Length = 1362 | | | |
| r0s0-180 | | Leptomycin resistance protein, pmd1, Schizosaccharomyces pombe. Length = 1362 | | 959–1009 | Transmembrane pump that removes FB1 from the cytoplasm as a means of protection against its toxic activity |
| r0c0-193 | | Leptomycin resistance protein, pmd1, Schizosaccharomyces pombe. Length = 1362 | | 885–945 | Transmembrane pump that removes FB1 from the cytoplasm as a means of protection against its toxic activity |
| r0s0-330 | | Leptomycin resistance protein, pmd1, Schizosaccharomyces pombe. Length = 1362 | | 1024–1110 | Transmembrane pump that removes FB1 from the cytoplasm as a means of protection against its toxic activity |
| Loc0-129 | S20548 | Leptomycin resistance protein, pmd1, Schizosaccharomyces pombe. Length = 1362 | .0082 | 949–988 | Transmembrane pump that removes FB1 from the cytoplasm as a means of protection against its toxic activity |
| r0h1-262 | | Leptomycin resistance protein, pmd1, Schizosaccharomyces pombe. Length = 1362 | | 1135–1218 | Transmembrane pump that removes FB1 from the cytoplasm as a means of protection against its toxic activity |
| i0c0-116 | e219956 | ATP binding cassette multidrug transporter, *Emericella nidulans* Length = 1466 | | 1026–1114 | Transmembrane pump that removes FB1 from the cytoplasm as a means of protection against its toxic activity |

TABLE 3

| Cloned Bands | Homology, Comments | Predicted function | Predicted Product |
|---|---|---|---|

1. Transmembrane pump (P-glycoprotein homolog)

| | | | |
|---|---|---|---|
| r0g1-420<br>g0s0-142<br>l0c0-129<br>r0s0-180<br>r0c0-193<br>r0s0-330<br>r0h1-262<br>i0c0-116 | Homology to Leptomycin resistance protein, Pmd1, *Schizosaccharomyces pombe*, Length = 1362, or other ABC transporter gene family member. { } All 9 bands show homology to members of the ABC transporter superfamily. | FB1 Pump: Transmembrane pump that removes FB1 from the cytoplasm as a means of protection against its toxicity | (structure of FB1)<br><br>FB1 exclusion from cell (proposed) |

2. Small Molecule Permease

| | | | |
|---|---|---|---|
| r0v0-239<br>r0w0-205<br>p0t0-308.4<br>r0w0-424?<br>w0h0-268? | Homology to choline transport protein, yeast Length = 563 { } Two bands (r0w0-205 and p0t0-308) contig with each other. | 2-OP permease: Transport of 2-OP and/or AP1 into the cytoplasm | (structures)<br><br>AP1 permease activity (proposed) |

3. Flavin Monooxygenase (EC 1.14.13.22)

TABLE 3-continued

| Cloned Bands | Homology, Comments | Predicted function | Predicted Product |
|---|---|---|---|
| m1a0-388 | Homology to cyclohexanone monooxygenase., Acinetobacter. Oxidation of ketone resulting in carbon-carbon bond breakage to form aldehyde. Utilizes NAD+ or NADP+ | 2-OP monooxygenase: Intracellular oxidation of 2-OP1 to a hydroxy aldehyde (HA-1) plus acetic acid | Hydroxy aldehyde (proposed) structure with OH, CH₃, OH, CH₃, OH groups and terminal CHO; plus $CH_3COO^-$ |
| | | 4. Aldehyde dehydrogenase | |
| k0n0-235 | Homology to aldehyde dehydrogenase (*Nicotiana tabacum*); Length = 542 | HA-1 deydrogense: Oxidation of aldehyde product of FMO to a hydroxy carboxylic acid (HCA-1) | Hydroxy-carboxylic acid (proposed) structure with OH, CH₃, OH, CH₃, OH groups and terminal $COO^-$ |

Using sequence derived from each clone, a partial cDNA was obtained by 3' and 5' RACE-PCR (Chenchik et al. (1995) *CLONTECHniquesX*1:5–8); Chenchik et al. (1996) in *A Laboratory Guide to RNA: Isolation, Analysis, and Synthesis,* ed. Krieg (Wiley-Liss, Inc.), pp. 273–321. A RACE cloning kit from Clontech was used to obtain the RACE amplicons. Briefly, poly A+ RNA is transcribed to make first strand cDNA using a "ock-docking" poly T, cDNA synthesis primer, the second strand is synthesized, and the Marathon cDNA adaptor is ligated to both ends of the ds cDNA. Diluted template is then used with the Marathon adapter primer and in separate reactions either a 5' Gene Specific Primer (GSP) or a 3'GSP is used to produce the 3' or 5' RACE amplicon. After characterization of the RACE product(s) and sequencing, full-length cDNAs may be generated by 1) end-to-end PCR using distal 5' and 3' GSPs with the adapter-ligated ds cDNA as template, or 2) the cloned 5' and 3'-RACE fragments may be digested with a restriction enzyme that cuts uniquely in the region of overlap, and the fragments isolated and ligated. Subsequently, the RACE-generated full-length cDNAs from 1) and 2) may be cloned into a suitable vector.

EXAMPLE 6

Pichia Expression of Degradative Enzymes

For cloning into *Pichia pastoris* expression vector, pPicZalphaA, oligonucleotide primers were designed that contain a 22 bp overlap of the 5' end (sense strand) and 3' end (antisense strand), respectively of the open reading frame of the degradative nucleotide of interest, including the stop codon. In addition, each oligo has a 5' extension with digestible restriction sites that allows cloning of the amplified insert in-frame both into EcoRI/NotI digested pPicZalphaA. pPicZalphaA is an *E. coli* compatible Pichia expression vector containing a functional yeast alpha-factor secretion signal and peptide processing sites, allowing high efficiency, inducible secretion into the culture medium of Pichia. After the generation of the 5' and 3' RACE products, the resulting band was cloned into EcoRI/NotI digested pPicZalphaA plasmid.

Pichia can be transformed as described in Invitrogen Manual, Easy Select™ Pichia Expression Kit, Version B, #161219, with the enzyme polynucleotide of interest with either an intron (negative control, no expression) or without an intron (capable of making an active protein). The Pichia culture fluids and pellets are assayed for enzyme activity as described earlier. The six day culture fluids from the same cultures are used to spike with crude fungal enzyme for positive controls.

The sample 50 µl cell pellets are resuspended in 150 µl cold 50 mM Na-phosphate, pH8.0 and divided into two fresh 500 UL tubes. One tube is kept on ice with no treatment, the pellet suspension, and one tube is used for lysis. An equal volume of 0.1 mm zirconia-silica beads is added to each tube. The tubes are BeadBeat™ for 15 seconds then cooled on ice 5 minutes. This is repeated three times. The crude lysate is then transferred to another tube for assay or lysate suspension. The TLC assays are performed as follows:
1) pellet suspensions ("PELL"); 10 uL
2) lysate suspensions ("LYS"); 10 uL
3) media controls-mixed 5 uL media with 5 uL crude fungal enzyme (if available); 10 uL
4) positive control-used crude fungal enzyme undiluted; 10 uL
5) substrate control-used 50 mM Na-phosphate, pH8.0; 10 uL cofactor (if required) is added to each reaction mixture
incubate 10 uL each sample+10 uL $^{14}$C-substrate (fumonisin, metabolite, or other potential substrate) (1 mg/nL, pH8) at room temperature for 6 days
spot 1.0 uL onto C18 and C60 TLC plates
develop C18 plates in MeOH:4% KCl (3:2)
develop C60 plates in $CHCl_3$:MeOH:$CH_3COOH$:$H_2O$ (55:36:8:1)
air-dry plates
expose plates to PhosphorScreen 2–3 days
use Storm PhosphorImager (Molecular Dynamics) to develop images

EXAMPLE 7

Expression of Degradative Enzymes in *E. coli*

A vector for expressing the enzymes in *E. coli* is a prokaryotic glutathione S-transferase (GST) fusion vector for inducible, high-level intracellular expression of genes or gene fragments as fusions with *Schistosoma japonicum* GST. GST gene fusion vectors include the following features: a lac promoter for inducible, high-level expression; an internal lac Iq gene for use in any *E. coli* host; and the thrombin factor Xa or PreScission Protease recognition sites for cleaving the desired protein from the fusion product. The insert of interest is cloned into the 5' EcoRI site and a 3' NotI site allowing in-frame expression of the fusion peptide. The generation of such an insert is described in the previous example.

*E. coli* is transformed with the vector containing the coding sequence for the degradative enzyme as described in BRL catalogue, Life Technologies, Inc., catalogue; Hanahan (1983) *J. Mol. Biol.* 166:557; Jessee et al. (1984) *J. Focus* 6:4; King et al. (1986) *Focus* 8:1, and hereby incorporated by reference. The transformed *E. coli* is induced by addition of IPTG (isopropyl b-D-thiogalactopyranoside). Samples of soluble extract and Samples of insoluble inclusion bodies are tested for enzyme activity as described in Example 7.

EXAMPLE 8

Transformation and Regeneration of Transgenic Plants

Immature maize embryos from greenhouse donor plants are bombarded with a plasmid containing the fumonisin-degradation/transporter enzyme nucleotide sequences operably linked to a ubiquitin promoter (FIG. 2). This plasmid also contains the selectable marker gene PAT (Wohlleben et al. (1988) *Gene* 70:25–37) that confers resistance to the herbicide Bialaphos. The preferred construct for expression in maize is the nucleotide sequence of the degradative enzyme either fused to the barley alpha amylase signal sequence or organellar targeting sequence, or left intact for expression in the cytoplasm.Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the fumonisin-degradation/transporter enzyme operably linked to the ubiquitin promoter is made. This plasmid DNA also contains a PAT selectable marker. The plasmid is precipitated onto 1.1 $\mu$m (average diameter) tungsten pellets using a $CaCl_2$ precipitation procedure as follows:

100 $\mu$l prepared tungsten particles in water

10 $\mu$l (1 $\mu$g) DNA in TrisEDTA buffer (1 $\mu$g total)

100 $\mu$l 2.5 M $CaCl_2$

10 $\mu$l 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored for the expression of a fumonisin-degrading/transporter protein.

APPENDIX

272 V

| Ingredient | Amount | Unit |
|---|---|---|
| D-I $H_2O$ | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:
@ = Add after bringing up to volume
Dissolve ingredients in polished D-I $H_2O$ in sequence
Adjust to pH 5.6
Bring up to volume with polished D-I $H_2O$ after adjusting pH
Sterilize and cool to 60° C.
= Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.
Total Volume (L) = 1.00

288 J

| Ingredient | Amount | Unit |
|---|---|---|
| D-I $H_2O$ | 950.000 | Ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| 0.1 mM Abscisic Acid | 1.000 | ml |
| Bialaphos 1 mg/ml # | 3.000 | ml |

Directions:
@ = Add after bringing up to volume
Dissolve ingredients in polished D-I $H_2O$ in sequence
Adjust to pH 5.6
Bring up to volume with polished D-I $H_2O$ after adjusting pH

288 J

| Ingredient | Amount | Unit |
|---|---|---|

Sterilize and cool to 60° C.
Add 3.5 g/L of Gelrite for cell biology.
= Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.
Total Volume (L) = 1.00

560 R

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:
@ = Add after bringing up to volume
# = Add after sterilizing and cooling to temp.
Dissolve ingredients in D-I $H_2O$ in sequence
Adjust to pH 5.8 with KOH
Bring up to volume with D-I $H_2O$
Sterilize and cool to room temp.
Total Volume (L) = 1.00

560 Y

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@ = Add after bringing up to volume
# = Add after sterilizing and cooling to temp.
Dissolve ingredients in D-I $H_2O$ in sequence
Adjust to pH 5.8 with KOH
Bring up to volume with D-I $H_2O$
Sterilize and cool to room temp.
Autoclave less time because of increased sucrose
Total Volume (L) = 1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A microorganism having stably incorporated at least one expression cassette comprising a promoter active in said microorganism operably linked to a nucleotide sequence, wherein:
   a) said microorganism is a bacterium or a fungus;
   b) said microorganism is heterologous to said nucleotide sequence; and
   c) said nucleotide sequence is selected from the group consisting of the nucleotide sequence set forth in SEQ ID NO: 6 or 7.

2. The microorganism of claim 1, wherein said expression cassette is stably incorporated into the genome of said microorganism.

3. A microorganism having stably incorporated at least one expression cassette comprising a promoter active in said microorganism operably linked to a nucleotide sequence, wherein said microorganism is heterologous to said nucleotide sequence and wherein:
   a) said nucleotide sequence has at least 90% identity to the nucleotide sequence set forth in SEQ ID NO: 6 or 7; and,
   b) expression of said sequence reduces the pathogenicity of a fungus producing fumonisin.

4. The microorganism of claim 3, wherein said nucleotide sequence encodes the amino acid sequence set forth in SEQ ID NO: 8.

5. A microorganism having stably incorporated at least one expression cassette comprising a nucleotide sequence, wherein:

a) said microorganism is a bacterium or a fungus;

b) said nucleotide sequence is operably linked to a promoter that is active in said microorganism;

c) said promoter is heterologous to the nucleotide sequence; and, d) said sequence is selected from the group consisting of the nucleotide sequence set forth in SEQ ID NO: 6 or 7.

6. The microorganism of claim 5, wherein said expression cassette is stably integrated into the genome of said microorganism.

7. A microorganism having stably incorporated at least one expression cassette comprising a nucleotide sequence, wherein:

a) said microorganism is a bacterium or a fungus;

b) said nucleotide sequence is operably linked to a promoter that is active in said microorganism;

c) said promoter is heterologous to said nucleotide sequence;

d) said nucleotide sequence encodes the amino acid sequence set forth in SEQ ID NO: 8; and, e) expression of said sequence reduces the pathogenicity of a fungus producing fumonisin.

8. The microorganism of claim 7, wherein said expression cassette is stably integrated into the genome of the microorganism.

9. A microorganism having stably incorporated at least one expression cassette comprising a nucleotide sequence, wherein:

a) said microorganism is a bacterium or a fungus;

b) said nucleotide sequence is operably linked to a promoter that is active in said microorganism;

b) said promoter is heterologous to the nucleotide sequence;

c) said nucleotide sequence has at least 90% identity to the nucleotide sequence set forth in SEQ ID NO: 6 or 7; and, d) expression of said sequence reduces the pathogenicity of a fungus producing fumonisin.

10. An expression cassette comprising a nucleotide sequence having at least 90% identity to the nucleotide sequence of SEQ ID NO:6, wherein said nucleotide sequence encodes a protein that retains permease activity and wherein said nucleotide sequence is operably linked to a promoter that drives expression in a microorganism, wherein said microorganism is a bacterium or fungus.

11. The expression cassette of claim 10, wherein said nucleotide sequence is set forth in SEQ ID NO: 6.

12. An expression cassette comprising a nucleotide sequence having at least 90% identity to the nucleotide sequence set forth in SEQ ID NO: 7, wherein said nucleotide sequence retains permease activity and wherein said nucleotide sequence is operably linked to a promoter that drives expression in a microorganism, wherein said microorganism is a bacterium or a fungus.

13. The expression cassette of claim 12, wherein said sequence comprises the nucleotide sequence set forth in SEQ ID NO: 7.

14. A microorganism which is a bacterium or a fungus, said microorganism having stably incorporated at least one DNA construct comprising a promoter active in said microorganism operably linked to a nucleotide sequence having at least 90% identity to the nucleotide sequence set forth in SEQ ID NO:7, wherein said nucleotide sequence retains permease activity and wherein said promoter is heterologous to said nucleotide sequence.

15. The microorganism of claim 14, wherein said sequence comprises the nucleotide sequence set forth in SEQ ID NO:7.

16. A microorganism which is a bacterium or a fungus, said microorganism having stably incorporated at least one nucleotide sequence having at least 90% identity to the nucleotide sequence set forth in SEQ ID NO:7, wherein:

a) said nucleotide sequence is operably linked to a promoter active in said microorganism;

b) said nucleotide sequence is heterologous to the microorganism; and c) said sequence retains permease activity.

17. The microorganism of claim 16, wherein said sequence comprises the nucleotide sequence set forth in SEQ ID NO: 7.

18. A method of producing a polypeptide useful in degrading fumonisin, said method comprising:

a) culturing the microorganism of claim 1; and, b) purifying the polypeptide encoded by said nucleotide sequence.

19. A method of producing a polypeptide useful in degrading fumonisin, said method comprising:

a) culturing the microorganism of claim 5; and, b) purifying the polypeptide encoded by said nucleotide sequence.

20. The microorganism of claim 3, wherein said nucleotide sequence has at least 95% identity to the nucleotide sequence set forth in SEQ ID NO:6 or 7.

21. The microorganism of claim 9, wherein said nucleotide sequence has at least 95% identity to the nucleotide sequence set forth in SEQ ID NO:6 or 7.

* * * * *

UNITED STATES PATENT AND TRADEMARK OFFICE
CERTIFICATE OF CORRECTION

PATENT NO.     : 6,534,291 B1
DATED          : March 18, 2003
INVENTOR(S)    : Duvick et al.

It is certified that error appears in the above-identified patent and that said Letters Patent is hereby corrected as shown below:

Title page,
Item [56], OTHER PUBLICATIONS, "Chen et al." reference, "1998" should read -- 1989 --.
"Rakin et al." reference, "(21)" should read -- (2) --.

Column 67,
Line 35, "b)" should read -- c) --;
Line 37, "c)" should read -- d) --;
Line 40, "d)" should read -- e) --.

Signed and Sealed this

Twenty-ninth Day of July, 2003

JAMES E. ROGAN
*Director of the United States Patent and Trademark Office*

SEQUENCE LISTING

<160> NUMBER OF SEQ ID NOS: 11

<210> SEQ ID NO 1
<211> LENGTH: 1691
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: flavin monooxygenase with intron

<400> SEQUENCE: 1

```
atgtcggcca ccagcaactc cagaggcgat tgttccgtcg catgcgacgc catcatcgtt      60
ggagccggcc tcagcggcat ctctgctgtg tacaaattgc gaaagctcag actcaacgcc     120
aaaatcttcg agggagcccc cgattttggc ggcgtctggc actggaaccg ctaccctggc     180
gctcgtgttg attcggagac gcccttctac caactgaaca ttcccgaagt atggaaagac     240
tggacctggt cttgccgcta tcctgaccag aaagagttgc tgtcatatgt tcaccactgt     300
gacaagatcc ggggcttgag aaaagacgtc tacttcggag ctgaggtggt tgatgcgcgg     360
tatgccgaga atctgggcac ctggactgtc aagacgtcgg ctgccatgt tgcgacggca     420 aagtatctca ttctcgctac ggggttgctc cacaggaagc acactcccgc actccccggc     480
```

-continued

```
ctcgccgatt tcaacgggaa ggtgattcat tcgagtgcct ggcacgaaga cttcgacgca      540
gagggccaga gagtcgccgt catcggtgcc ggggccacaa gcatccagat tgttcaggag      600
ttggccaaga aggctgacca ggtaaccatg tttatgcgaa ggccgagcta ttgtctgccc      660
atgcggcaac gaacgatgga taggaacgaa cagacagcct ggaaggccta ctacccacg       720 ctgtttgaag cgagtcgaaa gtctcggatt ggattcccgg tccaggcacc gtcggttggc      780
atctttgaag tcagccccga gcagcgggag gcctatttcg aagagttgtg ggagcgtggg      840
gcctttaatt ttcttgcttg ccagtaccga aagtcatgg ttgacaaaaa ggccaaccga       900
ctggtctatg acttctgggc caaaaagact cgatctcgta tcgtcaatcc ggcaaagaga      960
gatctcatgg ctcctctgga gccgccgtac tggttcggta ccaagcgctc cccactggag     1020
agcgactact acgaaatgct ggacaagccg agcgtcgaaa ttgtgaatct agaacaatcg     1080
cccattgtgg ctgttacaaa gacaggtgtg ctcttgagtg acggcagcaa gagggaatgc     1140
gacacgatcg tgctggcgac gggtttcgac agtttcactg gctcgtgagt gtgctcgatc     1200
atggctccga gtccggacgt ttggctgacc ttgaaagatt gacacatatg ggcttgaaaa     1260 acaagcacg agtggacctg aaggaggtgt ggaaagatgg catatctact tatatgggag      1320
tcttctctca tggcttcccc aatgccttct tcgtcgccac ggctcaagcc ccgaccgtcc     1380
tttccaacgg cccaacgatc atagaaaccc aagtcgactt gatcgccgat acaattgcaa     1440
agttggaggc cgagcacgcc acgtccgttg aggcgacgaa atcagcacaa gaggcatggt     1500
cgattatgat tgccaagatg aacgagcaca ctctgttccc cttgacggat tcgtggtgga     1560
ctggaggcaa catccctggg aaagcaacac gtgctttaac cttcataggc gggattgctc     1620
tctatgagca gatctgtcaa gagaaggtgg ccaattggga tgggtttgat gtgcttcatg     1680
ctccctgcta a                                                          1691

<210> SEQ ID NO 2
<211> LENGTH: 1638
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: flavin monooxygenase, fully spliced

<400> SEQUENCE: 2
atgtcggcca ccagcaactc cagaggcgat tgttccgtcg catgcgacgc catcatcgtt       60
ggagccggcc tcagcggcat ctctgctgtg tacaaattgc gaaagctcag actcaacgcc      120
aaaatcttcg agggagcccc cgattttggc ggcgtctggc actggaaccg ctaccctggc      180
gctcgtgttg attcggagac gcccttctac caactgaaca ttcccgaagt atggaaagac      240
tggacctggt cttgccgcta tcctgaccag aaagagttgc tgtcatatgt tcaccactgt      300
gacaagatcc ggggcttgag aaaagacgtc tacttcggag ctgaggtggt tgatgcgcgg      360
tatgccagag atctgggcac ctggactgtc aagacgtcgg ctggccatgt tgcgacggca      420
aagtatctca ttctcgctac ggggttgctc cacaggaagc acactcccgc actcccggc       480 ctcgccgatt tcaacgggaa ggtgattcat tcgagtgcct ggcacgaaga cttcgacgca      540
gagggccaga gagtcgccgt catcggtgcc ggggccacaa gcatccagat tgttcaggag      600
ttggccaaga aggctgacca ggtaaccatg tttatgcgaa ggccgagcta ttgtctgccc      660
atgcggcaac gaacgatgga taggaacgaa cagacagcct ggaaggccta ctacccacg       720 ctgtttgaag cgagtcgaaa gtctcggatt ggattcccgg tccaggcacc gtcggttggc      780
```

```
atctttgaag tcagccccga gcagcgggag gcctatttcg aagagttgtg ggagcgtggg      840
gcctttaatt ttcttgcttg ccagtaccga gaagtcatgg ttgacaaaaa ggccaaccga      900
ctggtctatg acttctgggc caaaaagact cgatctcgta tcgtcaatcc ggcaaagaga      960
gatctcatgg ctcctctgga gccgccgtac tggttcggta ccaagcgctc cccactggag     1020
agcgactact acgaaatgct ggacaagccg agcgtcgaaa ttgtgaatct agaacaatcg     1080
cccattgtgg ctgttacaaa gacaggtgtg ctcttgagtg acggcagcaa gagggaatgc     1140
gacacgatcg tgctggcgac gggtttcgac agtttcactg gctcattgac acatatgggc     1200
ttgaaaaaca gcacggagt ggacctgaag gaggtgtgga agatggcat atctacttat       1260 atgggagtct tctctcatgg cttccccaat gccttcttcg tcgccacggc tcaagccccg     1320
accgtccttt ccaacggccc aacgatcata gaaacccaag tcgacttgat cgccgataca     1380
attgcaaagt tggaggccga gcacgccacg tccgttgagg cgacgaaatc agcacaagag     1440
gcatggtcga ttatgattgc caagatgaac gagcacactc tgttcccctt gacggattcg     1500
tggtggactg gaggcaacat ccctgggaaa gcaaacgtg ctttaacctt cataggcggg      1560
attgctctct atgagcagat ctgtcaagag aaggtggcca attgggatgg gtttgatgtg     1620
cttcatgctc cctgctaa                                                    1638
```

<210> SEQ ID NO 3
<211> LENGTH: 545
<212> TYPE: PRT
<213> ORGANISM: Exophiala spinifera

<400> SEQUENCE: 3

```
Met Ser Ala Thr Ser Asn Ser Arg Gly Asp Cys Ser Val Ala Cys Asp
  1               5                  10                  15

Ala Ile Ile Val Gly Ala Gly Leu Ser Gly Ile Ser Ala Val Tyr Lys
             20                  25                  30

Leu Arg Lys Leu Arg Leu Asn Ala Lys Ile Phe Glu Gly Ala Pro Asp
         35                  40                  45

Phe Gly Gly Val Trp His Trp Asn Arg Tyr Pro Gly Ala Arg Val Asp
     50                  55                  60

Ser Glu Thr Pro Phe Tyr Gln Leu Asn Ile Pro Glu Val Trp Lys Asp
 65                  70                  75                  80

Trp Thr Trp Ser Cys Arg Tyr Pro Asp Gln Lys Glu Leu Leu Ser Tyr
                 85                  90                  95

Val His His Cys Asp Lys Ile Arg Gly Leu Arg Lys Asp Val Tyr Phe
            100                 105                 110

Gly Ala Glu Val Val Asp Ala Arg Tyr Ala Arg Asp Leu Gly Thr Trp
        115                 120                 125

Thr Val Lys Thr Ser Ala Gly His Val Ala Thr Ala Lys Tyr Leu Ile
    130                 135                 140

Leu Ala Thr Gly Leu Leu His Arg Lys His Thr Pro Ala Leu Pro Gly
145                 150                 155                 160

Leu Ala Asp Phe Asn Gly Lys Val Ile His Ser Ser Ala Trp His Glu
                165                 170                 175

Asp Phe Asp Ala Glu Gly Gln Arg Val Ala Val Ile Gly Ala Gly Ala
            180                 185                 190

Thr Ser Ile Gln Ile Val Gln Glu Leu Ala Lys Lys Ala Asp Gln Val
        195                 200                 205

Thr Met Phe Met Arg Arg Pro Ser Tyr Cys Leu Pro Met Arg Gln Arg
```

```
                210                 215                 220
Thr Met Asp Arg Asn Glu Gln Thr Ala Trp Lys Ala Tyr Tyr Pro Thr
225                 230                 235                 240

Leu Phe Glu Ala Ser Arg Lys Ser Arg Ile Gly Phe Pro Val Gln Ala
                245                 250                 255

Pro Ser Val Gly Ile Phe Glu Val Ser Pro Glu Gln Arg Glu Ala Tyr
                260                 265                 270

Phe Glu Glu Leu Trp Glu Arg Gly Ala Phe Asn Phe Leu Ala Cys Gln
                275                 280                 285

Tyr Arg Glu Val Met Val Asp Lys Lys Ala Asn Arg Leu Val Tyr Asp
                290                 295                 300

Phe Trp Ala Lys Lys Thr Arg Ser Arg Ile Val Asn Pro Ala Lys Arg
305                 310                 315                 320

Asp Leu Met Ala Pro Leu Glu Pro Pro Tyr Trp Phe Gly Thr Lys Arg
                325                 330                 335

Ser Pro Leu Glu Ser Asp Tyr Tyr Glu Met Leu Asp Lys Pro Ser Val
                340                 345                 350

Glu Ile Val Asn Leu Gln Ser Pro Ile Val Ala Val Thr Lys Thr
                355                 360                 365

Gly Val Leu Leu Ser Asp Gly Ser Lys Arg Glu Cys Asp Thr Ile Val
370                 375                 380

Leu Ala Thr Gly Phe Asp Ser Phe Thr Gly Ser Leu Thr His Met Gly
385                 390                 395                 400

Leu Lys Asn Lys His Gly Val Asp Leu Lys Glu Val Trp Lys Asp Gly
                405                 410                 415

Ile Ser Thr Tyr Met Gly Val Phe Ser His Gly Phe Pro Asn Ala Phe
                420                 425                 430

Phe Val Ala Thr Ala Gln Ala Pro Thr Val Leu Ser Asn Gly Pro Thr
                435                 440                 445

Ile Ile Glu Thr Gln Val Asp Leu Ile Ala Asp Thr Ile Ala Lys Leu
450                 455                 460

Glu Ala Glu His Ala Thr Ser Val Glu Ala Thr Lys Ser Ala Gln Glu
465                 470                 475                 480

Ala Trp Ser Ile Met Ile Ala Lys Met Asn Glu His Thr Leu Phe Pro
                485                 490                 495

Leu Thr Asp Ser Trp Trp Thr Gly Gly Asn Ile Pro Gly Lys Ala Thr
                500                 505                 510

Arg Ala Leu Thr Phe Ile Gly Gly Ile Ala Leu Tyr Glu Gln Ile Cys
                515                 520                 525

Gln Glu Lys Val Ala Asn Trp Asp Gly Phe Asp Val Leu His Ala Pro
                530                 535                 540

Cys
545

<210> SEQ ID NO 4
<211> LENGTH: 1464
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: aldehyde dehydrogenase, fully spliced cDNA

<400> SEQUENCE: 4
atggttcttt cgcctgacga atacaagagt gaactcttca tcaacaatga attcgtctcc    60
```

```
tccaagggt ccgagagatt aacgctcacg aacccgtggg acgaatccac cgttgccact    120
gatgttcacg tggccaacgc ggccgatgtc gacagtgcag tagccgcttc ggtgcaggcg    180
gtcaaaaagg gcccatggaa gaagttcaca ggtgcacaac gcgcggcgtg catgcttaag    240
ttcgcggacc tcgccgagaa gaacgccgag aagctcgctc gtctggagtc gctgcccacc    300
ggtagaccgg tgtcgatgat cactcatttc gacattccaa acatggtctc cgtgtttcgc    360
tactatgcag gctgggccga caagatcgcc ggaaagacct ttcccgagga caacggcaag    420
ccgaattggc gttacgagcc gatgggggtg tgtgctggta ttgccagctg gaacgcgact    480
tttctttacg tcggctggaa gatagccccc gccctcgccg ccggctgctc cttcatcttc    540
aaagcctcgg agaaatcccc gctgggcgtt ctgggcctcg ctcctctctt cgcagaagcc    600
ggattccctc ctggagtcgt gcagttcctc actggagcac gagtgacggg tgaagcattg    660
gcgtcgcaca tggacattgc gaagatcagc ttcacaagat ctgtcggcgg tggccgcgcc    720
gtcaagcaag caacactcaa gtccaacatg aagcgcgtca ctctagaact gggggaaaag    780
ccaaccatcg tcttcaacga agctcctctc gaacggcagt cggggggaatc ggcaaaggat    840 ttctcaaaat tcgggcaaat ttgggtcccc ccctcctgtt tgctagtgca atggggaaat    900
ttagcggaga aattccatgg agtccgtcat ggctcatttg gaggctgtca gagatggctt    960
ggccagaacc cattggaacc caagaggacg catggtccct cgtcgacaa gtcccagtac    1020 gacagagtct tgggtaacat tgacgttggc aaggataccg cgcagctcct cactggcgtt    1080
ggtagaaagg gcgacaaggg attcgcgatt gaaccgacga tatttgtcaa tcccaaacca    1140
ggcagcaaaa tttggtttga ggagatcttt ggccccgtct tgtccattaa gacgttcaag    1200
acggaagaag aggccattga gattgccaat gacacgactt atgggctagc ctcggtcatt    1260
tataccaaat ctctcaacag gggtctccgt gtctcgtcgg cgctcgagac cggtggcgtc    1320
tcgatcaact tccccttat ccccgagaca caaactccgt tggcggcat gaaacaatcg    1380 ggctcaggca gagagctagg cgaagaaggg ctcaaggcgt acttggagcc caagaccatt    1440
aatatccacg tcaacataga gtga                                             1464
```

<210> SEQ ID NO 5
<211> LENGTH: 487
<212> TYPE: PRT
<213> ORGANISM: Exophiala spinifera

<400> SEQUENCE: 5

Met Val Leu Ser Pro Asp Glu Tyr Lys Ser Glu Leu Phe Ile Asn Asn
1               5                   10                  15

Glu Phe Val Ser Ser Lys Gly Ser Glu Arg Leu Thr Leu Thr Asn Pro
            20                  25                  30

Trp Asp Glu Ser Thr Val Ala Thr Asp Val His Val Ala Asn Ala Ala
        35                  40                  45

Asp Val Asp Ser Ala Val Ala Ala Ser Val Gln Ala Val Lys Lys Gly
    50                  55                  60

Pro Trp Lys Lys Phe Thr Gly Ala Gln Arg Ala Ala Cys Met Leu Lys
65                  70                  75                  80

Phe Ala Asp Leu Ala Glu Lys Asn Ala Glu Lys Leu Ala Arg Leu Glu
                85                  90                  95

Ser Leu Pro Thr Gly Arg Pro Val Ser Met Ile Thr His Phe Asp Ile
            100                 105                 110

Pro Asn Met Val Ser Val Phe Arg Tyr Tyr Ala Gly Trp Ala Asp Lys
        115                 120                 125

-continued

```
Ile Ala Gly Lys Thr Phe Pro Glu Asp Asn Gly Lys Pro Asn Trp Arg
    130                 135                 140
Tyr Glu Pro Met Gly Val Cys Ala Gly Ile Ala Ser Trp Asn Ala Thr
145                 150                 155                 160
Phe Leu Tyr Val Gly Trp Lys Ile Ala Pro Ala Leu Ala Ala Gly Cys
                165                 170                 175
Ser Phe Ile Phe Lys Ala Ser Glu Lys Ser Pro Leu Gly Val Leu Gly
                180                 185                 190
Leu Ala Pro Leu Phe Ala Glu Ala Gly Phe Pro Pro Gly Val Val Gln
                195                 200                 205
Phe Leu Thr Gly Ala Arg Val Thr Gly Glu Ala Leu Ala Ser His Met
    210                 215                 220
Asp Ile Ala Lys Ile Ser Phe Thr Arg Ser Val Gly Gly Arg Ala
225                 230                 235                 240
Val Lys Gln Ala Thr Leu Lys Ser Asn Met Lys Arg Val Thr Leu Glu
                245                 250                 255
Leu Gly Glu Lys Pro Thr Ile Val Phe Asn Glu Ala Pro Leu Glu Arg
                260                 265                 270
Gln Ser Gly Glu Ser Ala Lys Asp Phe Ser Lys Phe Gly Gln Ile Trp
            275                 280                 285
Val Pro Pro Ser Cys Leu Leu Val Gln Trp Gly Asn Leu Ala Glu Lys
    290                 295                 300
Phe His Gly Val Arg His Gly Ser Phe Gly Cys Gln Arg Trp Leu
305                 310                 315                 320
Gly Gln Asn Pro Leu Glu Pro Lys Arg Thr His Gly Pro Phe Val Asp
                325                 330                 335
Lys Ser Gln Tyr Asp Arg Val Leu Gly Asn Ile Asp Val Gly Lys Asp
                340                 345                 350
Thr Ala Gln Leu Leu Thr Gly Val Gly Arg Lys Gly Asp Lys Gly Phe
            355                 360                 365
Ala Ile Glu Pro Thr Ile Phe Val Asn Pro Lys Pro Gly Ser Lys Ile
    370                 375                 380
Trp Phe Glu Glu Ile Phe Gly Pro Val Leu Ser Ile Lys Thr Phe Lys
385                 390                 395                 400
Thr Glu Glu Glu Ala Ile Glu Ile Ala Asn Asp Thr Thr Tyr Gly Leu
                405                 410                 415
Ala Ser Val Ile Tyr Thr Lys Ser Leu Asn Arg Gly Leu Arg Val Ser
                420                 425                 430
Ser Ala Leu Glu Thr Gly Gly Val Ser Ile Asn Phe Pro Phe Ile Pro
            435                 440                 445
Glu Thr Gln Thr Pro Phe Gly Met Lys Gln Ser Gly Ser Gly Arg
    450                 455                 460
Glu Leu Gly Glu Glu Gly Leu Lys Ala Tyr Leu Glu Pro Lys Thr Ile
465                 470                 475                 480
Asn Ile His Val Asn Ile Glu
                485
```

<210> SEQ ID NO 6
<211> LENGTH: 1764
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: permease, partially spliced cDNA

<400> SEQUENCE: 6

```
aactatggac tccagaccaa gtggatacgg cgagaaaggc gggacaaggc agacaacgaa      60
gaacacagag acggcggcgg caggtggtgc gtccgagtcc ctgaacgttc ctctggagaa     120
gaaacaattt ggcaccatca ccatcgtgtc cttggccttt gtgatttgca acagttgggc     180
tggtatctca ggcagtctcc agctcgccct actagcgggg gggcccgtca ctctccttta     240
cggcatccta atcagtactc tcgtctacat ctgcatcgct ttctcattag ccgaactgac     300
cagcgtctac ccgactgccg gtggccaata tcattttgcg tcgatcctgg caccaaaatc     360
aatcaatcgg agcatttcat acgtgtgcgg actcgtgtcg ttgctttcat ggatcgctat     420
cggaagctca gtgaccatga tacctgctca acagatcccg cgctgatag ccgcctatag      480
tcacacatac tcccaggatt cgtggcatgt cttcctcatc tacgagggag tcgcgctggt     540
ggtgctcttg ttcaacttgt ttgccctgaa agaaaccct tgggttcatg aaatcggatt      600
cggcctcacg atcgctctct tcgtgatctc ctttatcgcc attctagcgc ggtccaaccc     660
caaggctcca aactcacagg tatgactgc ttggagcaac tatactggct ggtccgacgg      720
cgtctgcttc atcctgggcc tttcgacatc ctgcttcatg ttcattggct tggacgcagc     780
aatgcatctg gctgaagaat gcacagatgc tgctcgtacg gtacccaaag cagtggtcag     840
tgcaatcata attggcttct gcaccgcctt tccatataca atcgcagttc tgtatggaat     900
tacagatctc gactctattc taagttccgc cggctatatt ccattcgaga caatgacgca     960
gtcccttcgg tcgctcagtt ttgcaacggt cctctcatgt ggcggtatcg tgatggcctt    1020
cttcgccctc aacgctgtac aagagactgc gtctcgactc acctggagct ttgcccggga    1080
caatgggctg gtattttcca ctcatctcga acgcattcat ccccgctggc aagttcctgt    1140
ttggtctcta ttcgcgacct ggggaattct ggccacatgc ggatgtatat ttctaggttc    1200
tagcacagct ttcaatgcct tggtcaattc cgccgttgta ctccagcaac tctccttcct    1260
gatcccaatc gccctactcc tctaccaaaa gcgagatcca aagttcttgc cgagcactcg    1320
tgcttttgtg ttaccgcgtg aatcgggtt tctggtcaat gtgctagcgg tggtcttcac     1380
gtccgtcacc actgtgtttt tcagcttccc actgaccgtg cctacggccg cgtcaaccat    1440
gaattacaca agtgcgatta taggcgttgc acttgctctt ggtgtcttga actgggtcgt    1500
gcatgccagg aagcattatc agggaccca cttggagctt gacggacggg tcgtcggagc     1560
agaatttcaa gttgggccat gaattggacg aaatggagac gcgtgtgcaa tgtcaaaaat    1620
tgctggggtg gtactgagag tctggattag ctgcaacgcg ggacaaccga gggtagaaca    1680
ctctgcaatc gagcaggaca atatcaatta ggcaachasv caaaaaaaaa aaaaaaaaa     1740
aaaaagcgg ccgctgaatt ctag                                           1764
```

<210> SEQ ID NO 7
<211> LENGTH: 1578
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: permease, fully spliced cDNA

<400> SEQUENCE: 7

```
atggactcca gaccaagtgg atacggcgag aaaggcggga caaggcagac aacgaagaac     60
acagagacgg cggcggcagg tggtgcgtcc gagtccctga acgttcctct ggagaagaaa    120
```

-continued

```
caatttggca ccatcaccat cgtgtccttg gcctttgtga tttgcaacag ttgggctggt      180
atctcaggca gtctccagct cgccctacta gcggggggc ccgtcactct cctttacggc       240
atcctaatca gtactctcgt ctacatctgc atcgctttct cattagccga actgaccagc      300
gtctacccga ctgccggtgg ccaatatcat tttgcgtcga tcctggcacc aaaatcaatc     360
aatcggagca tttcatacgt gtgcggactc gtgtcgttgc tttcatggat cgctatcgga     420
agctcagtga ccatgatacc tgctcaacag atcccggcgc tgatagccgc ctatagtcac     480
acatactccc aggattcgtg gcatgtcttc ctcatctacg agggagtcgc gctggtggtg     540
ctcttgttca acttgtttgc cctgaaaaga aacccttggg ttcatgaaat cggattcggc     600
ctcacgatcg ctctcttcgt gatctccttt atcgccattc tagcgcggtc caaccccaag     660
gctccaaact cacaggtatg gactgcttgg agcaactata ctggctggtc cgacggcgtc     720
tgcttcatcc tgggccttc gacatcctgc ttcatgttca ttggcttgga cgcagcaatg     780
catctggctg aagaatgcac agatgctgct cgtacggtac ccaaagcagt ggtcagtgca     840
atcataattg gcttctgcac cgccttcca tatacaatcg cagttctgta tggaattaca     900
gatctcgact ctattctaag ttccgccggc tatattccat tcgagacaat gacgcagtcc     960
cttcggtcgc tcagttttgc aacggtcctc tcatgtggcg gtatcgtgat ggccttcttc    1020
gccctcaacg ctgtacaaga gactgcgtct cgactcacct ggagctttgc ccgggacaat    1080
gggctggtat tttccactca ctcgaacgc attcatcccc gctggcaagt tcctgtttgg     1140
tctctattcg cgacctgggg aattctggcc acatgcggat gtatatttct aggttctagc    1200
acagctttca atgccttggt caattccgcc gttgtactcc agcaactctc cttcctgatc    1260
ccaatcgccc tactcctcta ccaaaagcga gatccaaagt tcttgccgag cactcgtgct    1320
tttgtgttac cgcgtggaat cgggtttctg gtcaatgtgc tagcggtggt cttcacgtcc    1380
gtcaccactg tgtttttcag cttcccactg accgtgccta cggccgcgtc aaccatgaat    1440
tacacaagtg cgattatagg cgttgcactt gctcttggtg tcttgaactg ggtcgtgcat    1500
gccaggaagc attatcaggg accccacttg gagcttgacg gacgggtcgt cggagcagaa    1560
tttcaagttg ggccatga                                                   1578
```

<210> SEQ ID NO 8
<211> LENGTH: 525
<212> TYPE: PRT
<213> ORGANISM: Exophiala spinifera

<400> SEQUENCE: 8

```
Met Asp Ser Arg Pro Ser Gly Tyr Gly Glu Lys Gly Gly Thr Arg Gln
 1               5                  10                  15

Thr Thr Lys Asn Thr Glu Thr Ala Ala Ala Gly Gly Ala Ser Glu Ser
             20                  25                  30

Leu Asn Val Pro Leu Glu Lys Lys Gln Phe Gly Thr Ile Thr Ile Val
         35                  40                  45

Ser Leu Ala Phe Val Ile Cys Asn Ser Trp Ala Gly Ile Ser Gly Ser
     50                  55                  60

Leu Gln Leu Ala Leu Leu Ala Gly Gly Pro Val Thr Leu Leu Tyr Gly
 65                  70                  75                  80

Ile Leu Ile Ser Thr Leu Val Tyr Ile Cys Ile Ala Phe Ser Leu Ala
                 85                  90                  95

Glu Leu Thr Ser Val Tyr Pro Thr Ala Gly Gly Gln Tyr His Phe Ala
            100                 105                 110
```

-continued

```
Ser Ile Leu Ala Pro Lys Ser Ile Asn Arg Ser Ile Ser Tyr Val Cys
        115                 120                 125

Gly Leu Val Ser Leu Leu Ser Trp Ile Ala Ile Gly Ser Ser Val Thr
130                 135                 140

Met Ile Pro Ala Gln Gln Ile Pro Ala Leu Ile Ala Ala Tyr Ser His
145                 150                 155                 160

Thr Tyr Ser Gln Asp Ser Trp His Val Phe Leu Ile Tyr Glu Gly Val
                165                 170                 175

Ala Leu Val Val Leu Leu Phe Asn Leu Phe Ala Leu Lys Arg Asn Pro
            180                 185                 190

Trp Val His Glu Ile Gly Phe Gly Leu Thr Ile Ala Leu Phe Val Ile
        195                 200                 205

Ser Phe Ile Ala Ile Leu Ala Arg Ser Asn Pro Lys Ala Pro Asn Ser
    210                 215                 220

Gln Val Trp Thr Ala Trp Ser Asn Tyr Thr Gly Trp Ser Asp Gly Val
225                 230                 235                 240

Cys Phe Ile Leu Gly Leu Ser Thr Ser Cys Phe Met Phe Ile Gly Leu
                245                 250                 255

Asp Ala Ala Met His Leu Ala Glu Glu Cys Thr Asp Ala Ala Arg Thr
            260                 265                 270

Val Pro Lys Ala Val Ser Ala Ile Ile Gly Phe Cys Thr Ala
        275                 280                 285

Phe Pro Tyr Thr Ile Ala Val Leu Tyr Gly Ile Thr Asp Leu Asp Ser
    290                 295                 300

Ile Leu Ser Ser Ala Gly Tyr Ile Pro Phe Glu Thr Met Thr Gln Ser
305                 310                 315                 320

Leu Arg Ser Leu Ser Phe Ala Thr Val Leu Ser Cys Gly Gly Ile Val
                325                 330                 335

Met Ala Phe Phe Ala Leu Asn Ala Val Gln Glu Thr Ala Ser Arg Leu
            340                 345                 350

Thr Trp Ser Phe Ala Arg Asp Asn Gly Leu Val Phe Ser Thr His Leu
        355                 360                 365

Glu Arg Ile His Pro Arg Trp Gln Val Pro Val Trp Ser Leu Phe Ala
370                 375                 380

Thr Trp Gly Ile Leu Ala Thr Cys Gly Cys Ile Phe Leu Gly Ser Ser
385                 390                 395                 400

Thr Ala Phe Asn Ala Leu Val Asn Ser Ala Val Val Leu Gln Gln Leu
                405                 410                 415

Ser Phe Leu Ile Pro Ile Ala Leu Leu Leu Tyr Gln Lys Arg Asp Pro
            420                 425                 430

Lys Phe Leu Pro Ser Thr Arg Ala Phe Val Leu Pro Arg Gly Ile Gly
        435                 440                 445

Phe Leu Val Asn Val Leu Ala Val Val Phe Thr Ser Val Thr Thr Val
    450                 455                 460

Phe Phe Ser Phe Pro Leu Thr Val Pro Thr Ala Ala Ser Thr Met Asn
465                 470                 475                 480

Tyr Thr Ser Ala Ile Ile Gly Val Ala Leu Ala Leu Gly Val Leu Asn
                485                 490                 495

Trp Val Val His Ala Arg Lys His Tyr Gln Gly Pro His Leu Glu Leu
            500                 505                 510

Asp Gly Arg Val Val Gly Ala Glu Phe Gln Val Gly Pro
        515                 520                 525
```

<210> SEQ ID NO 9
<211> LENGTH: 3999
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: p-glycoprotein, with introns

<400> SEQUENCE: 9

| | | | | | |
|---|---|---|---|---|---|
| tatttsccat | ctmckatgaa | tggcagatga | atcggagaaa | cctcgaccaa | accaagatgg | 60 |
| cagtgagtcg | tcctcacacc | ctcccccaga | aaaggaaacc | gaaggcagta | tttcagacta | 120 |
| tctacgaatc | ttcagatatg | ccgacaaata | cgactggact | ctcaatgtca | tcgcgctcat | 180 |
| ctgcgccatc | ggatccgggg | cttcccttcc | tctgatgtcg | atcatcttcg | gtagcttcac | 240 |
| caacaagttc | aacaattaca | attcgggcga | cgggagtcct | gaagcgttca | aggccgatgt | 300 |
| ggatcatttc | gtcctgtggt | tcgtctacct | ctttattggg | aagtttgtcc | tcacgtacgt | 360 |
| ttccacggct | gccattacca | tttcagctat | acgaaccact | cgaactcttc | gacgagtgtt | 420 |
| ccttgaatgc | accttgcggc | aagaggtctg | gcatttcgac | aagcagagca | atggagcaat | 480 |
| cgccactcag | gtcactacca | atggcaaccg | tatacaaaca | ggtattgccg | agaaattggt | 540 |
| ctttaccgtg | caggcacttt | caatgttctt | ttctgcattt | gtggtcgctt | tggcgtctca | 600 |
| gtggaagcta | gctttaatca | ccatgtccgt | catccctgcc | attttcctgg | tcaccggcat | 660 |
| ctgcatagca | attgatgccg | ctcaggaggc | caggatcacc | aggatctact | cacgcgccgc | 720 |
| tgtcctcgca | gaagaagtct | tatcatccat | ccggacagtc | catgctttct | acgcccagaa | 780 |
| gaaaatggtc | gaaaaatatg | atgtcttttt | gcagcaagca | caccaagaag | ggaagaagaa | 840 |
| atcgccaaat | tatgggggtct | tgttctcaac | tgagtacttt | tgcatttacg | ctgctatcgc | 900 |
| actgggcctt | ttgggaaagg | tttttcgcat | gtatcagaat | ggcgaggttg | ccgacgttgg | 960 |
| caaagtcttt | actgttgcct | ttccgtcacc | tttagcagcc | acgtccatct | caatgcttgc | 1020 |
| gccttcaggt | tcagtcgttt | accaacgccg | catcttcggc | ctccgaatta | ttcagtatca | 1080 |
| ttgacaaacc | cacgcagctc | gacccttctc | gacccttttt | ggaaagcagc | cagagggctg | 1140 |
| cttaggtcaa | attgagatcc | aaaacctggc | atttgcctac | ccctcccgac | catctgccca | 1200 |
| agtacttcga | gatttcaact | tgacaattcc | agctggcaag | acgacggccc | tcgtcggtgc | 1260 |
| atcaggtagc | ggcaaaagca | caatggtcgg | cttacttgaa | cggtggtatc | tgcccagttc | 1320 |
| ggggaggata | ttacttgatg | ggttggaact | gggacaatac | aatgtgaaat | ggctgagaag | 1380 |
| ccgcattcgc | ctcgttcaac | aggaacctgt | gttgtttcgt | ggcacaatct | tccagaacat | 1440 |
| tgccaacggt | ttcatggatg | agcaacgaga | tctgcctcgc | gaaaaacaaa | tggagcttgt | 1500 |
| gcaaaaagct | tgcaaagcag | caatgccgac | gtgttcatta | atgagcttcc | gaacggttat | 1560 |
| gagactgaag | ttggcgagcg | agccggagcc | ttgagtggag | gtcaacaagc | cgaattgcaa | 1620 |
| tcgcacgaag | tatcatatcg | gatcccaaga | tcctgttact | cgatgaagct | accagcgccc | 1680 |
| ttgacccgaa | ggcggagaaa | gtggtccagg | aggccttgaa | ccgagtgtcc | aaagaccgca | 1740 |
| ctactttggt | cattgcccac | aaactagcca | ctgtcatacg | actcactatt | agggcgaatt | 1800 |
| gggccctcta | gatgcatgct | cgagcggccg | ccagtgtgac | gaattgatgc | agaattcggc | 1860 |
| ttgtcattac | gccgcactgg | tgcgtgcaca | ggacctcggg | gctgacgaac | aagaagaaca | 1920 |
| tgagaagacc | ctgcacgaaa | aggcagcacg | agaagctgct | ggtgaacgac | cggcacttga | 1980 |
| gcgcactcac | accactgcca | catctcaagc | tggagacctg | gagaagcgga | aggtgccggt | 2040 |

-continued

```
cgggactttg ggctactcgc tcctaaaatg catcctaatc atgttctacg aacaaaaaaa      2100
tctctactgg tgcttcttgt tgtcaacaat agcggttctg atatgcgcgg ccacatttcc      2160
aggacaagcc cttttgtttt cgagattgct cactgtcttc gagttgagtg gtcatgcggc      2220
acaggaacgg gcagactttt atagtctgat gttctttgtc gtggctctag aaatctagt       2280 aggatatttc acgattggct ggacatgcaa cgttgtttca caagttgtca cccatcgcta      2340
tcgagccgaa atgttccaac gagtactgga tcaagacatc gaattcttcg acatcccgga     2400
gaatacttct ggtgctctca catcgcaact gtcagctcta cccacgcagt tgcaggagtt     2460
gatatcaaca aattcttctc atttttatcg ttgtcgtaca acatcctctc gagcagtgct     2520
ctagcactag cctatggatg gaaactgggc ctggtggttg tgtttggtgc acttccaccc     2580
ctgcttttgg ctggctacct cagaattcgt cttgagacga agctagaagc cggaaactcg     2640
gcaaactttg cagaaagtgc tgggcttgca agcgaagcag ttaccgcgat ccggaccgtc     2700
tcatctttga ctctcgaagg scatgttctc caacagtact cggacatgtt gagcaaggtc     2760
gtgctaagat catccaaagc tttggtttgg acgatgtttt ggttctcact gtcacagtcg     2820
atcgagtttc tggctatggc cctgggaatt ttggtatggg aagtcgacta ctggcttcag     2880
gtgaggtacg acacaactca attttatatc atcttcgtgg gcgttttgtt tgccggtcca     2940
agcagcagcc cagaagccga attactccac gagtcttacc aaggctcggt cggctgcgaa     3000
ctatatcctc tggctgcgga cattgaagcc gaccatccgc gaaacggagg agaacaagaa     3060
aaaagggcca gtgggtggat gccctgtcga cctcgaggac attgaattca ggtatcgtca     3120
acgtgattcg gctcgagttc tccgcggggt ttccatgaca atcgagccag gacaatttgt     3180
agcttatgtg ggcgcttctg gctgtggcaa gtcaacgttg atcgctttgt tggaacgatt     3240
ctacgacccg acctcgggcc gaatttcatt tgcacacgag aatattgcag aaatgtcgcc     3300
gcgcttgtac cgcggccata tgtctttggt ccaacaggaa cccacayttt accaaggctc     3360
cgttcgcgag aatgtgacgt tggccctcga agccgaatta tcagaagagc tttgtcaagg     3420
acgccttccc gcaaggccaa tgctttggat tttgtcatct ctttaccaga aggctttgaa     3480
acgccttgcg gctcaacgag ggatgcagtt ctccggcggg caacgacagc ggatcgccat     3540
cgcaagagca ttgattcgaa atccaaagct gttgctactt gacgaagcga cgtcagccct     3600
cgacacgcaa tcggaacgtc tggttcaagc tgccctcgat gaggcatcca cgagccgaac     3660
gacaatagca gtggcgcacc gactttccac tattcggaat gttgatgtta tttttgtgtt     3720
tgccaacggg agaatcgccg aaacgggcac tcacgcggaa ctacaacgac tgagaggaag     3780
atattacgag atgtgtttgg cacaatcttt agaccaagca tgagcgttca cagagaagcg     3840
gaaaagggcg gtgggatctt ttaggatagg tttagtggcg tgttacttac tacaggcgtt     3900
tggattcagg tacgacaact tgtacaataa gtagcataga gcatgtaatg aaagggtact     3960
cgtcccggaa aaaaaaaaaa aaaaaaaaa aaaaaaaa                              3999
```

<210> SEQ ID NO 10
<211> LENGTH: 3792
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: p-glycoprotein, fully spliced cDNA

<400> SEQUENCE: 10

```
atggcagatg aatcggagaa acctcgacca aaccaagatg gcagtgagtc gtcctcacac        60
```

```
cctcccccag aaaaggaaac cgaaggcagt atttcagact atctacgaat cttcagatat     120
gccgacaaat acgactggac tctcaatgtc atcgcgctca tctgcgccat cggatccggg     180
gcttcccttc ctctgatgtc gatcatcttc ggtagcttca ccaacaagtt caacaattac     240
aattcgggcg acgggagtcc tgaagcgttc aaggccgatg tggatcattt cgtcctgtgg     300
ttcgtctacc tctttattgg gaagtttgtc ctcacgtacg tttccacggc tgccattacc     360
atttcagcta tacgaaccac tcgaactctt cgacgagtgt tccttgaatg caccttgcgg     420
caagaggtct ggcatttcga caagcagagc aatggagcaa tcgccactca rgtcactacc     480
aatggcaacc gtatacaaac aggtattgcc gagaaattgg tctttaccgt gcaggcactt     540
tcaatgttct tttctgcatt tgtggtcgct ttggcgtctc agtggaagct agctttaatc     600
accatgtccg tcatccctgc catttttcctg gtcaccggca tctgcatagc aattgatgcc     660
gctcaggagg ccaggatcac caggatctac tcacgcgccg ctgtcctcgc agaagaagtc     720
ttatcatcca tccggacagt ccatgctttc tacgcccaga gaaaatggt cgaaaaatat     780 gatgtctttt tgcagcaagc acaccaagaa gggaagaaga atcgccaaa taatggsgtc     840 ttgttctcaa ctgagtactt tgcatttac gctgctatcg cactggcctt ttggaaaggt     900
tttcgcatgt atcagaatgg cgaggttgcc gacgttggca aagtctttac tgttgtcctt     960
tccgtcacct tagcagccac gtccatctca atgcttgcgc cttcaggttc agtcgtttac     1020
caacgccgca tcttcggctc cgaattattc agtatcattg acaaacccac gcagctcgac     1080
cctctcgacc cttctggaaa gcagccagag ggctgcctag gtcaaattga gatccaaaac     1140
ctggcatttg cctaccctc ccgaccatct gcccaagtac ttcgagattt caacttgaca     1200
attccagctg gcaagacgac ggccctcgtc ggtgcatcag gtagcggcaa agcacaatg     1260 gtcggcttac ttgaacggtg gtatctgccc agttcgggga ggatattact tgatgggttg     1320
gaactgggac aatacaatgt gaaatggctg agaagccgca ttcgcctcgt tcaacaggaa     1380
cctgtgttgt ttcgtggcac aatcttccag aacattgcca acggttcat ggatgagcaa     1440 cgagatctgc ctcgcgaaaa acaaatggag cttgtgcaaa aagcttgcaa agccagcaat     1500
ggcgacgtgt tcattaatga gcttccgaac ggttatgaga ctgaagttgg cgagcgagcc     1560
ggagccttga gtggaggtca acgacaacga attgcaatcg cacgaagtat catatcggat     1620
cccaagatcc tgttactcga tgaagctacc agcgcccttg acccgaaggc ggagaaagtg     1680
gtccaggagg ccttgaaccg agtgtccaaa gaccgcacta ctttggtcat tgcccacaaa     1740
ctagccactg tcaaaagtgc tggcaacatc gcagtcattt cccagggaa aatcgtcgag     1800 caaggcacac accacgaatt gatcgaattc ggctgtcatt acgccgcact ggtgcgtgca     1860
caggacctcg gggctgacga acaacaagaa catgagaaga ccctgcacga aaaggcagca     1920
cgagaagctg ctggtgaacg accggcactt gagcgcactc acaccactgc cacatctcaa     1980
gctggagacc tggagaagcg gaaggtgccg gtcgggactt ggggctactc gctcctaaaa     2040
tgcatcctaa tcatgttcta cgaacaaaaa aatctctact ggtgcttctt gttgtcaaca     2100
ataacggttc tgatatgcgc ggccacattt ccaggacaag ccctttttgtt ttcgagattg     2160 ctcactgtct tcgagttgag tggtcatgcg gcacaggaac gggcagactt ttatattctg     2220
atgttctttg tcgtggctct aggaaatcta gtaggatatt tcacgattgg ctggacatgc     2280
aacgttattt cacaagttgt cacccatcgc tatcaagccg caatgttcca acgagtactg     2340
gatcaagaca tcgaactcct cgacatcccg gagcaaattt ctggtgctct cacatcgcaa     2400
```

```
ctgtcagctc tacccacgca gttgcaagag ttgatatcag caaattttct catttatatc    2460
gttgtcggtc aacatcgtct cgagcagtgc tctaccacta gcctatggat ggaaactggg    2520
cctggtggtt gtgtttggtg cacttccacc cctgcttttg gctggctacc tcagaattcg    2580
tctagagacg aagctagaag ccggaaactc ggcaaacttt gcagaaagtg ctgggcttgc    2640
aagcgaagca gttaccgcga tccggaccgt ctcatctttg actctcgaag gccatgttct    2700
ccaacagtac tcggacatgt tgagcaaggt cttgctaaga tcatccaaag cttttggttt    2760
ggacgatgtt ttggttttca cttgtcacag tcgatggagt ttttggctat tgccctggga    2820
ttttgtattg cagtcgataa ttggcttcag gtgagtacga cacaactcaa ttttatatca    2880
tcttcgtggg cgttttgttt gccggtccaa gcagcagccc agtatttggc ttactccacg    2940
agttttacca aggctcggtc ggctgcgaac tatatcctct ggctgcggac attgaagccg    3000
accatccgcg aaacggagga gaacaagaaa aaaggcccag tgggtggatg ccctgtcgac    3060
ctcgaggaca ttgaattcag gtatcgtcaa cgtgattcgg ctcgagttct ccgcggggtt    3120
tccatgacaa tcgagccagg acaatttgta gcttatgtgg gcgcttctgg ctgtggcaag    3180
tcaacgttga tcgctttgtc ggaacgattc tacgacccga cctcgggccg aatttcattt    3240
gcacacgaga atattgcaga aatgtcgccg cgcttgtacc gcggccatat gtctttggtc    3300
caacaggaac ccacacttta ccaaggctcc gttcgcgaga atgtgacgtt ggccctcgaa    3360
gccgaattat cagaagagct ttgtcaagga cgccttcccg caaggccaat gctttggatt    3420
ttgtcatctc tttaccagaa ggctttgaaa cgccttgcgc tcaacgagg  atgcagttc    3480 tccggcgggc aacgacagcg gatcgccatc gcaagagcat tgattcgaaa tccaaagctg    3540
ttgctacttg acgaagcgac gtcagccctc gacacgcaat cggaacgtct ggttcaagct    3600
gccctcgatg aggcatccac gagccgaacg acaatagcag tggcgcaccg actttccact    3660
attcggaatg ttgatgttat ttttgtgttt gccaacggga gaatcgccga aacgggcact    3720
cacgcggaac tacaacgact gagaggaaga tattacgaga tgtgtttggc acaatcttta    3780
gaccaagcat ga                                                       3792
```

<210> SEQ ID NO 11
<211> LENGTH: 1263
<212> TYPE: PRT
<213> ORGANISM: Exophiala spinifera
<220> FEATURE:
<221> NAME/KEY: VARIANT
<222> LOCATION: 157
<223> OTHER INFORMATION: Xaa = Any Amino Acid

<400> SEQUENCE: 11

Met Ala Asp Glu Ser Glu Lys Pro Arg Pro Asn Gln Asp Gly Ser Glu
 1               5                  10                  15

Ser Ser Ser His Pro Pro Glu Lys Glu Thr Glu Gly Ser Ile Ser
            20                  25                  30

Asp Tyr Leu Arg Ile Phe Arg Tyr Ala Asp Lys Tyr Asp Trp Thr Leu
        35                  40                  45

Asn Val Ile Ala Leu Ile Cys Ala Ile Gly Ser Gly Ala Ser Leu Pro
     50                  55                  60

Leu Met Ser Ile Ile Phe Gly Ser Phe Thr Asn Lys Phe Asn Asn Tyr
 65                  70                  75                  80

Asn Ser Gly Asp Gly Ser Pro Glu Ala Phe Lys Ala Asp Val Asp His
                85                  90                  95

Phe Val Leu Trp Phe Val Tyr Leu Phe Ile Gly Lys Phe Val Leu Thr

```
            100                 105                 110
Tyr Val Ser Thr Ala Ala Ile Thr Ile Ser Ala Ile Arg Thr Thr Arg
            115                 120                 125
Thr Leu Arg Arg Val Phe Leu Glu Cys Thr Leu Arg Gln Glu Val Trp
            130                 135                 140
His Phe Asp Lys Gln Ser Asn Gly Ala Ile Ala Thr Xaa Val Thr Thr
145                 150                 155                 160
Asn Gly Asn Arg Ile Gln Thr Gly Ile Ala Glu Lys Leu Val Phe Thr
                165                 170                 175
Val Gln Ala Leu Ser Met Phe Phe Ser Ala Phe Val Ala Leu Ala
                180                 185                 190
Ser Gln Trp Lys Leu Ala Leu Ile Thr Met Ser Val Ile Pro Ala Ile
                195                 200                 205
Phe Leu Val Thr Gly Ile Cys Ile Ala Ile Asp Ala Ala Gln Glu Ala
            210                 215                 220
Arg Ile Thr Arg Ile Tyr Ser Arg Ala Ala Val Leu Ala Glu Glu Val
225                 230                 235                 240
Leu Ser Ser Ile Arg Thr Val His Ala Phe Tyr Ala Gln Lys Lys Met
                245                 250                 255
Val Glu Lys Tyr Asp Val Phe Leu Gln Gln Ala His Gln Glu Gly Lys
                260                 265                 270
Lys Lys Ser Pro Asn Asn Gly Val Leu Phe Ser Thr Glu Tyr Phe Cys
            275                 280                 285
Ile Tyr Ala Ala Ile Ala Leu Ala Phe Trp Lys Gly Phe Arg Met Tyr
            290                 295                 300
Gln Asn Gly Glu Val Ala Asp Val Gly Lys Val Phe Thr Val Val Leu
305                 310                 315                 320
Ser Val Thr Leu Ala Ala Thr Ser Ile Ser Met Leu Ala Pro Ser Gly
                325                 330                 335
Ser Val Val Tyr Gln Arg Arg Ile Phe Gly Ser Glu Leu Phe Ser Ile
                340                 345                 350
Ile Asp Lys Pro Thr Gln Leu Asp Pro Leu Asp Pro Ser Gly Lys Gln
            355                 360                 365
Pro Glu Gly Cys Leu Gly Gln Ile Glu Ile Gln Asn Leu Ala Phe Ala
            370                 375                 380
Tyr Pro Ser Arg Pro Ser Ala Gln Val Leu Arg Asp Phe Asn Leu Thr
385                 390                 395                 400
Ile Pro Ala Gly Lys Thr Thr Ala Leu Val Gly Ala Ser Gly Ser Gly
                405                 410                 415
Lys Ser Thr Met Val Gly Leu Leu Glu Arg Trp Tyr Leu Pro Ser Ser
                420                 425                 430
Gly Arg Ile Leu Leu Asp Gly Leu Glu Leu Gly Gln Tyr Asn Val Lys
                435                 440                 445
Trp Leu Arg Ser Arg Ile Arg Leu Val Gln Gln Glu Pro Val Leu Phe
            450                 455                 460
Arg Gly Thr Ile Phe Gln Asn Ile Ala Asn Gly Phe Met Asp Glu Gln
465                 470                 475                 480
Arg Asp Leu Pro Arg Glu Lys Gln Met Glu Leu Val Gln Lys Ala Cys
                485                 490                 495
Lys Ala Ser Asn Gly Asp Val Phe Ile Asn Glu Leu Pro Asn Gly Tyr
                500                 505                 510
Glu Thr Glu Val Gly Glu Arg Ala Gly Ala Leu Ser Gly Gly Gln Arg
            515                 520                 525
```

```
Gln Arg Ile Ala Ile Ala Arg Ser Ile Ile Ser Asp Pro Lys Ile Leu
    530                 535                 540
Leu Leu Asp Glu Ala Thr Ser Ala Leu Asp Pro Lys Ala Glu Lys Val
545                 550                 555                 560
Val Gln Glu Ala Leu Asn Arg Val Ser Lys Asp Arg Thr Thr Leu Val
                    565                 570                 575
Ile Ala His Lys Leu Ala Thr Val Lys Ser Ala Gly Asn Ile Ala Val
                580                 585                 590
Ile Ser Gln Gly Lys Ile Val Glu Gln Gly Thr His His Glu Leu Ile
            595                 600                 605
Glu Phe Gly Cys His Tyr Ala Ala Leu Val Arg Ala Gln Asp Leu Gly
        610                 615                 620
Ala Asp Glu Gln Gln Glu His Glu Lys Thr Leu His Glu Lys Ala Ala
625                 630                 635                 640
Arg Glu Ala Ala Gly Glu Arg Pro Ala Leu Glu Arg Thr His Thr Thr
                    645                 650                 655
Ala Thr Ser Gln Ala Gly Asp Leu Glu Lys Arg Lys Val Pro Val Gly
                660                 665                 670
Thr Leu Gly Tyr Ser Leu Leu Lys Cys Ile Leu Ile Met Phe Tyr Glu
            675                 680                 685
Gln Lys Asn Leu Tyr Trp Cys Phe Leu Leu Ser Thr Ile Thr Val Leu
        690                 695                 700
Ile Cys Ala Ala Thr Phe Pro Gly Gln Ala Leu Leu Phe Ser Arg Leu
705                 710                 715                 720
Leu Thr Val Phe Glu Leu Ser Gly His Ala Ala Gln Glu Arg Ala Asp
                    725                 730                 735
Phe Tyr Ile Leu Met Phe Phe Val Val Ala Leu Gly Asn Leu Val Gly
                740                 745                 750
Tyr Phe Thr Ile Gly Trp Thr Cys Asn Val Ile Ser Gln Val Val Thr
            755                 760                 765
His Arg Tyr Gln Ala Ala Met Phe Gln Arg Val Leu Asp Gln Asp Ile
        770                 775                 780
Glu Leu Leu Asp Ile Pro Glu Gln Ile Ser Gly Ala Leu Thr Ser Gln
785                 790                 795                 800
Leu Ser Ala Leu Pro Thr Gln Leu Gln Glu Leu Ile Ser Ala Asn Phe
                    805                 810                 815
Leu Ile Tyr Ile Val Val Gly Gln His Arg Leu Glu Gln Cys Ser Thr
                820                 825                 830
Thr Ser Leu Trp Met Glu Thr Gly Pro Gly Gly Cys Val Trp Cys Thr
            835                 840                 845
Ser Thr Pro Ala Phe Gly Trp Leu Pro Gln Asn Ser Ser Arg Asp Glu
        850                 855                 860
Ala Arg Ser Arg Lys Leu Gly Lys Leu Cys Arg Lys Cys Trp Ala Cys
865                 870                 875                 880
Lys Arg Ser Ser Tyr Arg Asp Pro Asp Arg Leu Ile Phe Asp Ser Arg
                    885                 890                 895
Arg Pro Cys Ser Pro Thr Val Leu Gly His Val Glu Gln Gly Leu Ala
                900                 905                 910
Lys Ile Ile Gln Ser Phe Trp Phe Gly Arg Cys Phe Gly Phe His Leu
            915                 920                 925
Ser Gln Ser Met Glu Phe Leu Ala Ile Ala Leu Gly Phe Cys Ile Ala
        930                 935                 940
```

-continued

```
Val Asp Asn Trp Leu Gln Val Ser Thr Thr Gln Leu Asn Phe Ile Ser
945                 950                 955                 960

Ser Ser Trp Ala Phe Cys Leu Pro Val Gln Ala Ala Ala Gln Tyr Leu
            965                 970                 975

Ala Tyr Ser Thr Ser Phe Thr Lys Ala Arg Ser Ala Ala Asn Tyr Ile
            980                 985                 990

Leu Trp Leu Arg Thr Leu Lys Pro Thr Ile Arg Glu Thr Glu Glu Asn
        995                 1000                1005

Lys Lys Lys Gly Pro Val Gly Gly Cys Pro Val Asp Leu Glu Asp Ile
        1010                1015                1020

Glu Phe Arg Tyr Arg Gln Arg Asp Ser Ala Arg Val Leu Arg Gly Val
1025                1030                1035                1040

Ser Met Thr Ile Glu Pro Gly Gln Phe Val Ala Tyr Val Gly Ala Ser
                1045                1050                1055

Gly Cys Gly Lys Ser Thr Leu Ile Ala Leu Ser Glu Arg Phe Tyr Asp
            1060                1065                1070

Pro Thr Ser Gly Arg Ile Ser Phe Ala His Glu Asn Ile Ala Glu Met
            1075                1080                1085

Ser Pro Arg Leu Tyr Arg Gly His Met Ser Leu Val Gln Gln Glu Pro
    1090                1095                1100

Thr Leu Tyr Gln Gly Ser Val Arg Glu Asn Val Thr Leu Ala Leu Glu
1105                1110                1115                1120

Ala Glu Leu Ser Glu Glu Leu Cys Gln Gly Arg Leu Pro Ala Arg Pro
            1125                1130                1135

Met Leu Trp Ile Leu Ser Ser Leu Tyr Gln Lys Ala Leu Lys Arg Leu
            1140                1145                1150

Ala Ala Gln Arg Gly Met Gln Phe Ser Gly Gly Gln Arg Gln Arg Ile
        1155                1160                1165

Ala Ile Ala Arg Ala Leu Ile Arg Asn Pro Lys Leu Leu Leu Leu Asp
        1170                1175                1180

Glu Ala Thr Ser Ala Leu Asp Thr Gln Ser Glu Arg Leu Val Gln Ala
1185                1190                1195                1200

Ala Leu Asp Glu Ala Ser Thr Ser Arg Thr Thr Ile Ala Val Ala His
            1205                1210                1215

Arg Leu Ser Thr Ile Arg Asn Val Asp Val Ile Phe Val Phe Ala Asn
            1220                1225                1230

Gly Arg Ile Ala Glu Thr Gly Thr His Ala Glu Leu Gln Arg Leu Arg
        1235                1240                1245

Gly Arg Tyr Tyr Glu Met Cys Leu Ala Gln Ser Leu Asp Gln Ala
    1250                1255                1260
```